(12) United States Patent
Liu et al.

(10) Patent No.: US 8,268,143 B2
(45) Date of Patent: *Sep. 18, 2012

(54) OXYGEN-EFFECT FREE ANALYTE SENSOR

(75) Inventors: Zenghe Liu, Alameda, CA (US);
Tianmei Ouyang, Fremont, CA (US);
Hyun Cho, Berkeley, CA (US);
Yohannes Goti, Oakland, CA (US);
Benjamin J. Feldman, Oakland, CA (US); Fei Mao, Fremont, CA (US);
Adam Heller, Austin, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 445 days.

This patent is subject to a terminal disclaimer.

(21) Appl. No.: 12/172,589

(22) Filed: Jul. 14, 2008

(65) Prior Publication Data
US 2009/0099434 A1   Apr. 16, 2009

Related U.S. Application Data

(63) Continuation-in-part of application No. 12/051,835, filed on Mar. 19, 2008, which is a continuation-in-part of application No. 11/503,519, filed on Aug. 10, 2006, which is a continuation of application No. 10/639,181, filed on Aug. 11, 2003, now Pat. No. 7,090,756, which is a continuation of application No. 09/712,452, filed on Nov. 14, 2000, now Pat. No. 6,605,201.

(60) Provisional application No. 60/165,565, filed on Nov. 15, 1999.

(51) Int. Cl.
*C12Q 1/32*    (2006.01)

(52) U.S. Cl. ......... 204/403.01; 204/403.02; 204/403.03; 204/403.04; 204/403.05; 204/403.06; 204/403.07; 204/403.08; 204/403.09; 204/403.12; 204/403.11

(58) Field of Classification Search . 204/403.01–403.15
See application file for complete search history.

(56) References Cited

U.S. PATENT DOCUMENTS
5,262,035 A    11/1993    Gregg et al.
(Continued)

FOREIGN PATENT DOCUMENTS
CA    2464572 A1    1/2004
(Continued)

OTHER PUBLICATIONS

Abruna, H. D. et al., "Rectifying Interfaces Using Two-Layer Films of Electrochemically Polymerized Vinylpyridine and Vinylbipyridine Complexes of Ruthenium and Iron on Electrodes," J. Am. Chem. Soc., vol. 103, No. 1, pp. 1-5 (Jan. 14, 1981).

(Continued)

*Primary Examiner* — Keith Hendricks
*Assistant Examiner* — Bach Dinh
(74) *Attorney, Agent, or Firm* — Edward J. Baba; Khin K. Chin; Bozicevic, Field & Francis LLP

(57) ABSTRACT

The present invention provides an electrochemical sensor having a sensing chemistry that operates substantially free of any "oxygen effect". The electrochemical sensors are useful in determining the level of an analyte in a biological sample from a subject. The present invention also provides sensor assemblies including the electrochemical sensors as well as methods of using the same.

38 Claims, 7 Drawing Sheets

U.S. PATENT DOCUMENTS

| | | | |
|---|---|---|---|
| 5,262,305 | A | 11/1993 | Heller et al. |
| 5,264,092 | A | 11/1993 | Skotheim et al. |
| 5,264,104 | A | 11/1993 | Gregg et al. |
| 5,264,105 | A | 11/1993 | Gregg et al. |
| 5,320,725 | A | 6/1994 | Gregg et al. |
| 5,356,786 | A | 10/1994 | Heller et al. |
| 5,378,628 | A | 1/1995 | Grätzel et al. |
| 5,393,903 | A | 2/1995 | Grätzel et al. |
| 5,410,059 | A | 4/1995 | Fraser et al. |
| 5,437,999 | A | 8/1995 | Diebold et al. |
| 5,463,057 | A | 10/1995 | Graetzel |
| 5,589,326 | A | 12/1996 | Deng et al. |
| 5,593,852 | A | 1/1997 | Heller |
| 5,665,222 | A | 9/1997 | Heller |
| 5,683,832 | A | 11/1997 | Bonhote |
| 5,789,592 | A | 8/1998 | Graetzel et al. |
| 5,804,049 | A | 9/1998 | Chan |
| 5,846,702 | A | 12/1998 | Deng et al. |
| 5,965,380 | A | 10/1999 | Heller |
| 5,972,199 | A | 10/1999 | Heller |
| 6,083,710 | A | 7/2000 | Heller |
| 6,103,033 | A | 8/2000 | Say et al. |
| 6,120,676 | A | 9/2000 | Heller et al. |
| 6,121,009 | A | 9/2000 | Heller |
| 6,134,461 | A | 10/2000 | Say et al. |
| 6,143,164 | A | 11/2000 | Heller et al. |
| 6,175,752 | B1 | 1/2001 | Say et al. |
| 6,245,988 | B1 | 6/2001 | Gratzel et al. |
| 6,262,264 | B1 | 7/2001 | Buck |
| 6,278,056 | B1 | 8/2001 | Sugihara et al. |
| 6,294,062 | B1 | 9/2001 | Buck et al. |
| 6,299,757 | B1 * | 10/2001 | Feldman et al. ............... 205/775 |
| 6,338,790 | B1 | 1/2002 | Feldman et al. |
| 6,352,824 | B1 | 3/2002 | Buck |
| 6,605,200 | B1 * | 8/2003 | Mao et al. ................. 204/403.14 |
| 6,605,201 | B1 | 8/2003 | Mao |
| 6,616,819 | B1 * | 9/2003 | Liamos et al. ........... 204/403.02 |
| 6,746,582 | B2 | 6/2004 | Heller et al. |
| 7,429,630 | B2 | 9/2008 | Liu et al. |
| 2004/0040840 | A1 * | 3/2004 | Mao et al. ................. 204/403.04 |
| 2005/0173245 | A1 * | 8/2005 | Feldman et al. ......... 204/403.01 |
| 2005/0199494 | A1 * | 9/2005 | Say et al. ................. 204/403.01 |
| 2008/0035479 | A1 | 2/2008 | Liu et al. |

FOREIGN PATENT DOCUMENTS

| | | |
|---|---|---|
| EP | 1 230 249 | 8/2002 |
| JP | 4-114012 | 4/1992 |
| WO | WO 98/35225 | 8/1998 |
| WO | WO 99/03868 | 1/1999 |
| WO | WO 99/45375 | 9/1999 |
| WO | WO 99/45387 | 9/1999 |
| WO | WO 99/56613 | 11/1999 |
| WO | WO 99/59218 | 11/1999 |
| WO | WO 99/67628 | 12/1999 |
| WO | WO 00/20626 | 4/2000 |
| WO | WO 03/098731 | 11/2003 |

OTHER PUBLICATIONS

Calvert et al., "Synthetic and Mechanistic Investigations of the Reductive Electrochemical Polymerization of Vinyl-Containing Complexes of Iron (II), Ruthenium(II), and Osmium(II)," Inorganic Chemistry, vol. 22, No. 15, 1983, pp. 2151-2162.

Cass, A. et al., "Ferricinum Ion as an Electron Acceptor for Oxido-Reductases," J. Electroanal. Chem., vol. 190, pp. 117-127 (1985).

Cass, A. et al., "Ferrocene-Mediated Enzyme Electrode for Amperometric Determination of Glucose", Anal. Chem., vol. 56, No. 4, pp. 667-671 (Apr. 1984).

Chen, C.Y. et al., "A Biocompatible Needle-Type Glucose Sensor Based on Platinum-Electroplated Carbon Electrode", Applied Biochemistry and Biotechnology, vol. 36, pp. 211-226 (1992).

Chen, C.Y. et al., "Amperometric Needle-Type Glucose Sensor based on a Modified Platinum Electrode with Diminished Response to Interfering Materials", Analytica Chimica Acta, vol. 265, pp. 5-14 (1992).

(Chit) Yu et al, Macromolecules, 1999, 32, pp. 5251-5256.

Csoregi, E. et al., "Design, Characterization, and One-Point in Vivo Calibration of a Subcutaneously Implanted Glucose Electrode," Anal. Chem., vol. 66, No. 19, pp. 31313138 (Oct. 1, 1994).

Csoregi, E. et al., "On-Line Glucose Monitoring by Using Microdialysis Sampling and Amperometric Detection Based on "Wired" Glucose Oxidase in Carbon Paste," Mikrochim. Acta., vol. 121, pp. 31-40 (1995).

Degani, Y. et al., "Direct Electrical Communication between Chemically Modified Enzymes and Metal Electrodes. 2. Methods for Bonding Electron-Transfer Relays to Glucose Oxidase and D-Amino-Acid Oxidase," J. Am. Chem. Soc., vol. 110, No. 8, pp. 2615-2620 (1988).

Degani, Y. et al., "Electrical Communication between Redox Centers of Glucose Oxidase and Electrodes via Electrostatically and Covalently Bound Redox Polymers," J. Am. Chem. Soc., vol. 111, pp. 23572358 (1989).

Degani, Y. et al., Direct Electrical Communication between Chemically Modified Enzymes and Metal Electrodes. 1. Electron Transfer from Glucose Oxidase to Metal Electrodes via Electron Relays, Bound Covalently to the Enzyme, J. Phys. Chem., vol. 91, No. 6, pp. 1285-1289 (1987).

Dicks, J. M., "Ferrocene modified polypyrrole with immobilised glucose oxidase and its application in amperometric glucose microbiosensors," Ann. Biol. clin., vol. 47, pp. 607-619 (1989).

Doherty, A.P. et al., "The Effect of the Nature of the Polymer Backbone on the Stability and the Analytical Response of Polymer-Modified Electrodes", Electroanalysis, vol. 7, No. 4, pp. 333-339 (1995).

Dupray et al, Inorg. Chem. 1996, 35, pp. 6299-6307.

Fieselmann, B. et al., "Synthesis, Electron Paramagnetic Resonance, and Magnetic Studies on Binuclear Bis(.eta..sup.5-cyclopentadienyl)titanium(III) Compounds with Bridging Pyrazolate, Biimidazolate, and Bibenzimidazolate Anions", Inorganic Chemistry, vol. 17, No. 8, pp. 2078-2084.

Fischer, H. et al., "Intramolecular Electron Transfer Mediated by 4,4'-Bipyridine and Related Bridging Groups", J. Am. Chem. Soc., vol. 98, No. 18, pp. 5512-5517 (Sep. 1, 1976).

Foulds, N. et al., "Enzyme Entrapment in Electrically Conducting Polymers," J. Chem. Soc., Faraday Trans I., vol. 82, pp. 1259-1264 (1986).

Foulds, N. et al., "Immobilization of Glucose Oxidase in Ferrocene-Modified Pyrrole Polymers," Anal. Chem., vol. 60, No. 22, pp. 2473-2478 (Nov. 15, 1988).

Gholamkhass et al. J. Phys. Chem. B 1997, 101, pp. 9010-9021.

Gregg, B. et al., "Cross-Linked Redox Gels Containing Glucose Oxidase for Amperometric Biosensor Applications," Analytical Chemistry, vol. 62, No. 3, pp. 258-263 (Feb. 1, 1990).

Gregg, B. et al., "Redox Polymer Films Containing Enzymes. 1. A Redox-Conducting Epoxy Cement: Synthesis, Characterization, and Electrocatalytic Oxidation of Hydroquinone," J. Phys. Chem., vol. 95, No. 15, pp. 5970-5975 (1991).

Haga, M., "Synthesis and Protonation-deprotonation Reactions of Ruthenium(II) Complexes Containing 2,2'-Bibenzimidazole and Related Ligands", Inorganica Chimica Acta, vol. 75, pp. 29-35 (1983).

Hale, P. et al., "A New Class of Amperometric Biosensor Incorporating a Polymeric Electron-Transfer Mediator," J. Am. Chem. Soc., vol. 111, No. 9, pp. 3482-3484 (1989).

Hedenmo et al., Analyst 1996, 121, pp. 1891-1895.

Heller, A., "Electrical Connection of Enzyme Redox Centers to Electrodes," J. Phys. Chem., vol. 96, No. 9, pp. 3579-3587 (1992).

Heller, A., "Electrical Wiring of Redox Enzymes," Acc. Chem. Res., vol. 23, No. 5, pp. 129-134 (1990).

Ianniello, R.M. et al. "Immobilized Enzyme Chemically Modified Electrode as an Amperometric Sensor", Anal. Chem., vol. 53, No. 13, pp. 2090-2095 (Nov. 1981).

Ikeda, T. et al., "Glucose oxidase-immobilized benzoquinone-carbon paste electrode as a glucose sensor," Agric. Biol. Chem., vol. 49, No. 2, (1 page—Abstract only) (1985).

Jönsson, G. et al., "An Amperometric Glucose Sensor Made by Modification of a Graphite Electrode Surface with Immobilized Glucose Oxidase and Adsorbed Mediator", Biosensors, vol. 1, pp. 355-368 (1985).

Katakis, I. et al., "Electrostatic Control of the Electron Transfer Enabling Binding of Recombinant Glucose Oxidase and Redox Polyelectrolytes," J. Am. Chem. Soc., vol. 116, No. 8, pp. 3617-3618 (1994).

Katakis, I. et al., "L-.alpha.-Glycerophosphate and L-Lactate Electrodes Based on the Electrochemical "Wiring" of Oxidases," Analytical Chemistry, vol. 64, No. 9, pp. 1008-1013 (May 1, 1992).

Kenausis, G. et al., "'Wiring' of glucose oxidase and lactate oxidase within a hydrogel made with poly(vinly pyridine) complexed with [Os(4,4'-dimethoxy-2,2'-bipyridine).sub.2 Cl].sup.+/2+," J. Chem. Soc., Faraday Trans., vol. 92, No. 20, pp. 4131-4136 (1996).

Maidan, R. et al., "Elimination of Electrooxidizable Interferant-Produced Currents in Amperometric Biosensors," Analytical Chemistry, vol. 64, No. 23, pp. 2889-2896 (Dec. 1, 1992).

Majumdar et al, J. Chem. Soc. Dalton Trans., 1998, pp. 1569-1574.

Ohara, T. et al., ""Wired" Enzyme Electrodes for Amperometric Determination of Glucose or Lactate in the Presence of Interfering Substances," Analytical Chemistry, vol. 66, No. 15, pp. 2451-2457 (Aug. 1, 1994).

Ohara, T. et al., "Glucose Electrodes Based on Cross-Linked [Os(bpy).sub.2 Cl].sup.+/2+ Complexed Poly(1-vinylimadazole) Films," Analytical Chemistry, vol. 65, No. 23, pp. 3512-3516 (Dec. 1, 1993).

Ohara, T., "Osmium Bipyridyl Redox Polymers Used in Enzyme Electrodes," Platinum Metals Rev., vol. 39, No. 2, pp. 54-62 (Apr. 1995).

Pickup, J. et al., "Potentially-implantable, amperometric glucose sensors with mediated electron transfer: improving the operating stability," Biosensors, vol. 4, No. 2, (1 page—Abstract only) (1989).

Pishko, M. et al., "Amperometric Glucose Microelectrodes Prepared Through Immobilization of Glucose Oxidase in Redox Hydrogels", Anal. Chem., vol. 63, No. 20, pp. 2268-2272 (Oct. 15, 1991).

Pollak, A. et al., "Enzyme Immobilization by Condensation Copolymerization into Cross-Linked Polyacrylamide Gels,"J. Am. Chem. Soc., vol. 102, No. 20, pp. 6324-6336 (1980).

Reeder, K. et al., "Solution-State Spin-Equilibrium Properties of the Tris[2-(2-pyridyl)imidazole]iron(II) and Tris[2-(2-pyridyl)benzimidazole]iron(II) Cations", Inorganic Chemistry, vol. 17, No. 4, pp. 1071-1075 (1978).

Sasso, S. et al., "Electropolymerized 1,2-Diaminobenzene as a Means to Prevent Interferences and Fouling and to Stabilize Immobilized Enzyme in Electrochemical Biosensors", Anal. Chem., vol. 62, No. 11, pp. 1111-1117 (Jun. 1, 1990).

Schalkhammer, T. et al., "Electrochemical Glucose Sensors on Permselective Non-conducting Substituted Pyrrole Polymers", Sensors and Actuators, vol. B4, pp. 273-281 (1991).

Schmehl et al., "The Effect of Redox Site Concentration on the Rate of Mediated Oxidation of Solution Substrates by a Redox Copolymer Film," J. Electroanal. Chem. 152, 1983, pp. 97-109.

Surridge et al., Electron and Counterion Diffusion Constants in Mixed-Valent Polymeric Osmium Bipyridine Films, The Journal of Physical Chemistry, vol. 98, No. 3, 1994, pp. 917-923.

Surridge et al., Site Dilution of Osmium Polypyridine Complexes in Three Electron-Hopping Conductive Polymer Films on Electrodes by Electrochemical Copolymerization of Osmium with Ruthenium and with Zinc Complexes, Inorganic Chemistry, vol. 29, No. 24, 1990, pp. 4950-4955.

Taylor, C. et al., "'Wiring' of glucose oxidase within a hydrogel made with polyvinyl imidazole complexed with [(Os-4,4'-dimethoxy-2,2'-bipyridine)Cl].sup.+/2+," Journal of Electroanalytical Chemistry, vol. 396, pp. 511-515 ( ) 1995).

Trojanowicz, M. et al., "Enzyme Entrapped Polypyrrole Modified Electrode for Flow-Injection Determination of Glucose," Biosensors & Bioelectronics, vol. 5, pp. 149-156 (1990).

Ye, L. et al., "High Current Density "Wired" Quinoprotein Glucose Dehydrogenase Electrode," Anal. Chem., vol. 65, No. 3, pp. 238-241 (Feb. 1, 1993).

Yildiz, A., "Evaluation of an Improved Thin-Layer Electrode", Analytical Chemistry vol. 40, No. 7, pp. 1018-1024 (Jun. 1968).

Park, et al. "Sol-Gel-based Amperometric Glucose Biosensor Incorporating an Osmium Redox Polymer as Mediator" Analytical Communications, 33:271-273 (Aug. 1996).

Orellana, et al. "Spectroscopic, Electrochemical, and Kinetic Characterization of New Ruthenium(II) Tris-chelates Containing Five-Membered Heterocyclic Moieties" Helvetica Chimica Acta, 1987, vol. 70, No. 8, p. 2073-2086.

Sugiyarto, et al. "Structural, Magnetic and Mössbauer Studies of Bis(2,6-bis(pyrazol-3-yl)pyridine)iron(II) Triflate and its Hydrates" Australian Journal of Chemistry, 1987, vol. 40, No. 5, p. 775-783.

* cited by examiner

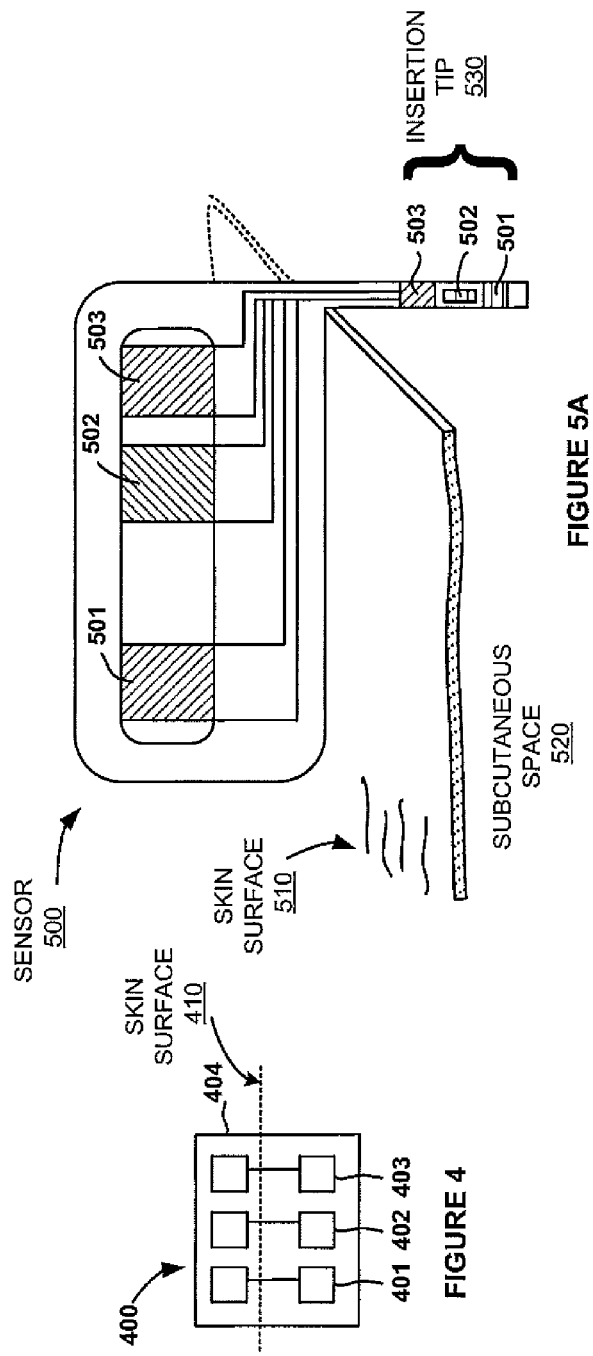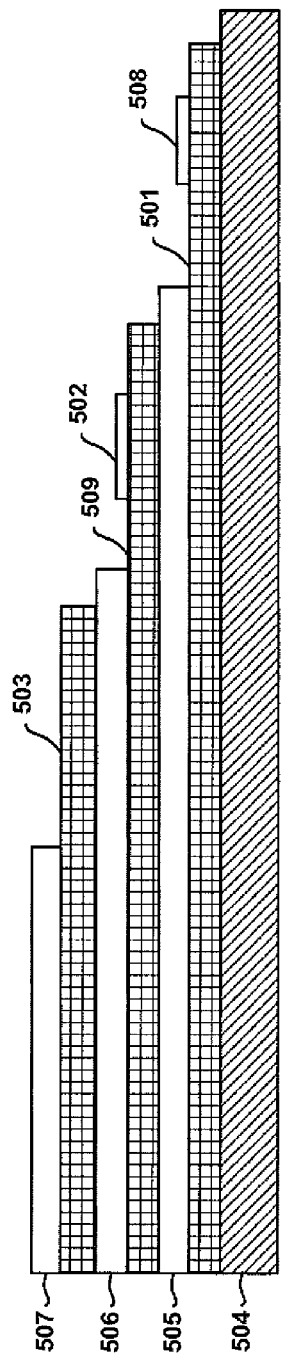

OXYGEN-EFFECT FREE ANALYTE SENSOR

CROSS-REFERENCE TO RELATED APPLICATIONS

This application is a continuation-in-part of U.S. patent application Ser. No. 12/051,835, filed Mar. 19, 2008, which is pending and is a continuation-in-part of U.S. patent application Ser. No. 11/503,519, filed Aug. 10, 2006, which is pending and which is a continuation of U.S. patent application Ser. No. 10/639,181, filed Aug. 11, 2003, issued as U.S. Pat. No. 7,090,756, which is a continuation of U.S. patent application Ser. No. 09/712,452, filed Nov. 14, 2000, issued as U.S. Pat. No. 6,605,201, which claim the benefit of priority of U.S. Provisional Patent Application Ser. No. 60/165,565, filed Nov. 15, 1999, which are incorporated herein by reference.

BACKGROUND

Enzyme-based biosensors are devices in which an analyte-concentration-dependent biochemical reaction signal is converted into a measurable physical signal, such as an optical or electrical signal. Such biosensors are widely used in the detection of analytes in clinical, environmental, agricultural and biotechnological applications. Analytes that can be measured in clinical assays of fluids of the human body include, for example, glucose, lactate, cholesterol, bilirubin and amino acids. The detection of analytes in biological fluids, such as blood, is important in the diagnosis and the monitoring of many diseases.

Biosensors that detect analytes via electrical signals, such as current (amperometric biosensors) or charge (coulometric biosensors), are of special interest because electron transfer is involved in the biochemical reactions of many important bioanalytes. For example, the reaction of glucose with glucose oxidase involves electron transfer from glucose to the enzyme to produce gluconolactone and reduced enzyme. In an example of an amperometric glucose biosensor, glucose is oxidized by oxygen in the body fluid via a glucose oxidase-catalyzed reaction that generates gluconolactone and hydrogen peroxide, then the hydrogen peroxide is electrooxidized and correlated to the concentration of glucose in the body fluid.

Some biosensors are designed for implantation in a living animal body, such as a mammalian or a human body, merely by way of example. In an implantable amperometric biosensor, the working electrode is typically constructed of a sensing layer, which is in direct contact with the conductive material of the electrode, and a diffusion-limiting membrane layer on top of the sensing layer. The sensing layer typically includes an enzyme, an optional enzyme stabilizer such as bovine serum albumin (BSA), and a crosslinker that crosslinks the sensing layer components. Alternatively, the sensing layer consists of an enzyme, a polymeric redox mediator, and a crosslinker that crosslinks the sensing layer components, as is the case in "wired-enzyme" biosensors.

Under normal physiological conditions, oxygen concentration in the extracellular fluid of the human body is approximately 40 mm Hg. Non-lethal concentrations can range from about 10 to about 1000 mm Hg. (Guyton & Hall, Textbook of *Medical Physiology*, 10$^{th}$ Ed. p. 5). Given such a wide variation in oxygen concentration in the glucose sensing environment, it is desirable to manufacture a glucose sensor that operates independently of oxygen.

Embodiments of the invention address this need.

SUMMARY OF THE INVENTION

Embodiments of the invention provide an electrochemical sensor, including a glucose biosensor, having a sensing chemistry that operates substantially free of any "oxygen effect". The use of glucose dehydrogenase in glucose sensors reduces problems associated with the "oxygen-effect". The electrochemical sensors are useful in determining the level of an analyte in a biological sample from a subject. Embodiments of the invention also provide sensor assemblies including the electrochemical sensors as well as methods of using the same.

These and other objects, advantages, and features of the invention will become apparent to those persons skilled in the art upon reading the details of the invention as more fully described below.

BRIEF DESCRIPTION OF THE DRAWINGS

A detailed description of various aspects, features and embodiments of the invention is provided herein with reference to the accompanying drawings, which are briefly described below. The drawings are illustrative and are not necessarily drawn to scale. The drawings illustrate various aspects or features of the invention and may illustrate one or more embodiment(s) or example(s) of the invention in whole or in part. A reference numeral, letter, and/or symbol that is used in one drawing to refer to a particular element or feature maybe used in another drawing to refer to a like element or feature.

FIG. 4 shows a schematic diagram of an embodiment of an analyte sensor according to the embodiments of the invention.

FIGS. 5A-5B show a perspective view and a cross sectional view, respectively of another embodiment an analyte sensor.

DETAILED DESCRIPTION

Figure 1:
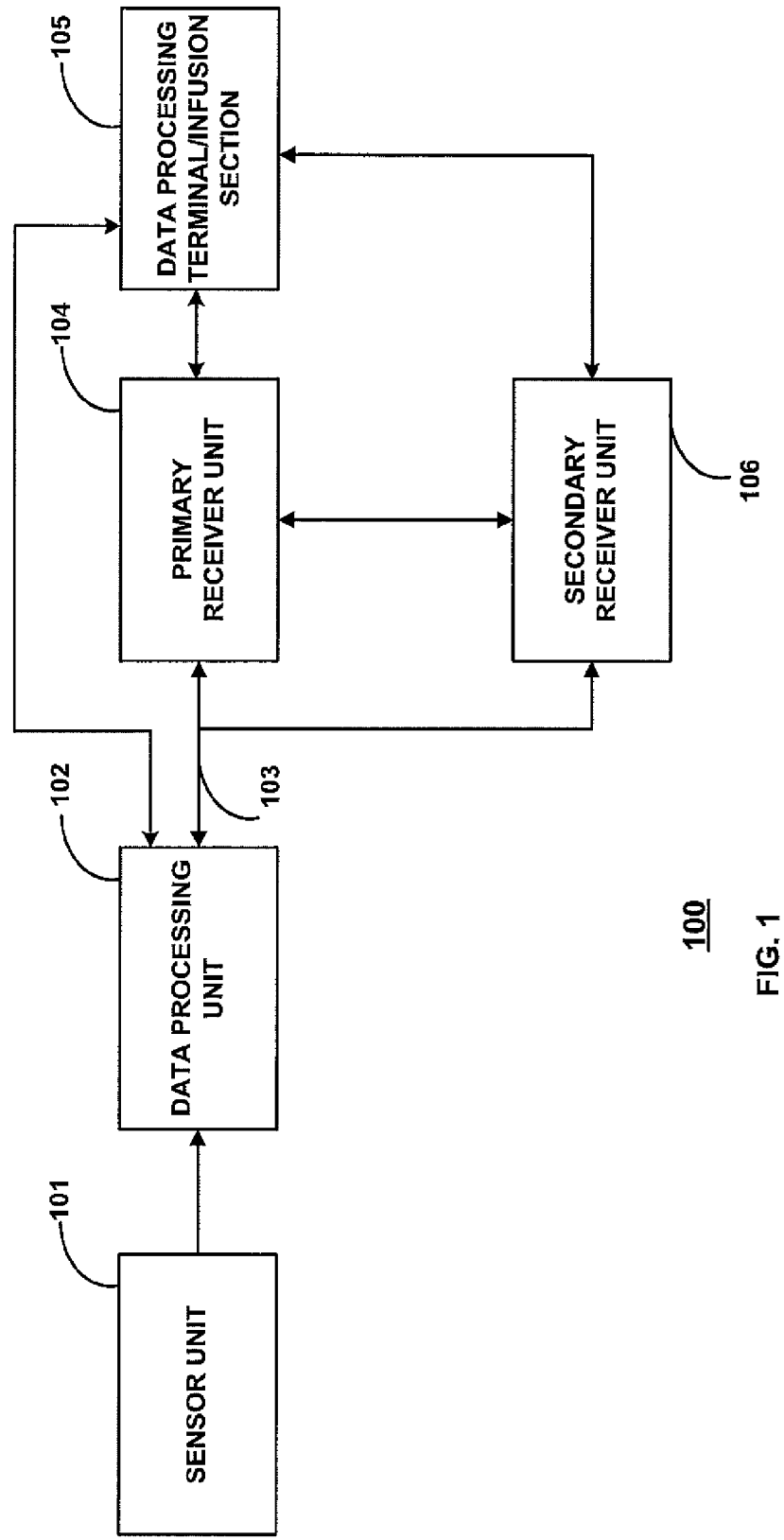
FIG. 1 shows a block diagram of an embodiment of a data monitoring and management system according to the embodiments of the invention.

Before the embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is to be noted that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

The publications discussed herein are provided solely for their disclosure prior to the filing date of the application. Nothing herein is to be construed as an admission that the embodiments of the invention is not entitled to antedate such publication by virtue of prior invention. Further, the dates of publication provided may be different from the actual publication dates which may need to be independently confirmed.

Various terms are described below to facilitate an understanding of an embodiment of the invention. It will be understood that a corresponding description of these various terms applies to corresponding linguistic or grammatical variations or forms of these various terms. It will also be understood that aspects of the invention are not limited to the terminology used herein, or the descriptions thereof, for the description of particular embodiments. Merely by way of example, an embodiment of the invention is not limited to particular analytes, bodily or tissue fluids, blood or capillary blood, or sensor designs or usages, unless implicitly or explicitly understood or stated otherwise, as such may vary.

Embodiments of the invention provide electrochemical analyte sensors, such as glucose biosensors, that include a sensing chemistry deposited in the working electrode that operates substantially free of any oxygen-effect. Generally, in such sensors, oxygen is not needed to generate a signal and oxygen does not interfere with the sensing current. As described in more detail below, the use of an analyte responsive dehydrogenase, such as glucose dehydrogenase, overcomes the problems associated with the "oxygen-effect". In addition, by reducing the effect of oxygen, the analyte measurements from the electrochemical sensors are improved.

Although mediator/oxidase-based biosensors of the art eliminate the dependence on oxygen concentration for the extended linear range of the sensor, oxygen-related drawbacks still exist. For example, some mediators are not as efficient at shuttling electrons with the enzyme as the oxygen molecule. In addition, any oxygen in the sample solution can effectively compete with osmium or other metals for electrons.

Therefore, mediator/oxidase-based biosensors may generate inaccuracies as a result of the "oxygen-effect". These inaccuracies become more serious when the substrate concentration is at a low concentration level (e.g., glucose concentration less than 70 mg/dL).

To address the interference resulting from the varying oxygen concentration or so-called "oxygen effect", an analyte responsive dehydrogenase, such as glucose dehydrogenase (GDH) is used to replace oxygen-sensitive oxidases such as glucose oxidase. In addition, the analyte response dehydrogenase may further be complexed with a co-factor that provides for electron transfer a redox mediator. Suitable co-factors include, but are not limited to, Flavin adenine dinucleotide (FAD), nicotinamide adenine dinucleotide (NAD), pyrroloquinoline quinone (PQQ), and the like. Glucose dehydrogenase, whose coenzyme include PQQ, NAD, or FAD, has comparatively less interaction with oxygen. Therefore, the resultant analyte sensor is substantially unaffected by variable oxygen concentrations in the sample. Herein, such a sensor may be in the form of a subcutaneously implantable continuous in vivo sensor.

Generally, any dehydrogenase may be used in embodiments of the invention. A dehydrogenase is an enzyme that oxidizes a substrate by transferring one or more protons and a pair of electrons to an acceptor, usually NAD/NADP or a flavin coenzyme such as FAD or FMN. Exemplary dehydrogenases include, but are not limited to, aldehyde dehydrogenase, acetaldehyde dehydrogenase, alcohol dehydrogenase, glutamate dehydrogenase, lactate dehydrogenase, pyruvate dehydrogenase, glucose-6-phosphate dehydrogenase (GDH), glyceraldehyde-3-phosphate dehydrogenase, isocitrate dehydrogenase, alpha-ketoglutarate dehydrogenase, succinate dehydrogenase, malate dehydrogenase, and the like.

Embodiments of the electrochemical analyte sensors include a working electrode, a counter electrode, an analyte response dehydrogenase optionally complexed with a co-factor disposed on the working electrode, where the analyte response dehydrogenase optionally complexed with a co-factor reacts with an analyte of interest resulting in generation of free electrons; and a redox polymer disposed proximate to the working electrode, where the redox polymer conducts the free electrons to the working electrode. In some embodiments, at least a portion of the sensor is adapted to be subcutaneously positioned in a subject. In some embodiments, the sensor further comprises a reference electrode.

Specific elements of the electrochemical analyte sensor are described in further detail below.

Transition Metal Complex

In at least some instances, the redox polymer of the electrochemical sensor further comprises a transition metal complex having one or more of the following characteristics: redox potentials in a particular range, the ability to exchange electrons rapidly with electrodes, the ability to rapidly transfer electrons to or rapidly accept electrons from an enzyme to accelerate the kinetics of electrooxidation or electroreduction of an analyte in the presence of an enzyme or another analyte-specific redox catalyst. For example, a redox mediator may accelerate the electrooxidation of glucose in the presence of a analyte response dehydrogenase optionally complexed with a co-factor, such as GDH optionally complexed with a co-factor including FAD, a process that can be useful for the selective assay of glucose in the presence of other electrochemically oxidizable species. Compounds having the formula 1 are examples of transition metal complexes of the embodiments of the invention.

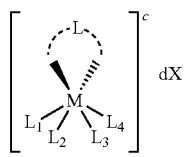

M is a transition metal and is typically iron, cobalt, ruthenium, osmium, or vanadium. Ruthenium and osmium are particularly suitable for redox mediators.

L is a bidentate ligand containing at least one imidazole ring. One example of L is a 2,2'-biimidazole having the following structure 2:

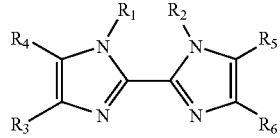

$R_1$ and $R_2$ are substituents attached to two of the 2,2'-biimidazole nitrogens and are independently substituted or unsubstituted alkyl, alkenyl, or aryl groups. Generally, $R_1$ and $R_2$ are unsubstituted C1 to C12 alkyls. Typically, $R_1$ and $R_2$ are unsubstituted C1 to C4 alkyls. In some embodiments, both $R_1$ and $R_2$ are methyl.

$R_3$, $R_4$, $R_5$, and $R_6$ are substituents attached to carbon atoms of the 2,2'-biimidazole and are independently —H, —F, —Cl, —Br, —I, —NO$_2$, —CN, —CO$_2$H, —SO$_3$H, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_3$ and $R_4$ in combination or $R_5$ and $R_6$ in combination independently form a saturated or unsaturated 5- or 6-membered ring. An example of this is a 2,2'-bibenzoimidazole derivative. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Generally, $R_3$, $R_4$, $R_5$, and $R_6$ are independently —H or unsubstituted alkyl groups. Typically, $R_3$, $R_4$, $R_5$, and $R_6$ are —H or unsubstituted C1 to C12 alkyls. In some embodiments, $R_3$, $R_4$, $R_5$, and $R_6$ are all —H.

Another example of L is a 2-(2-pyridyl)imidazole having the following structure 3:

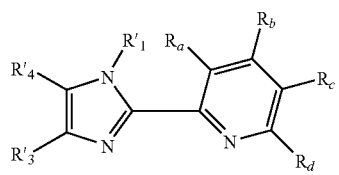

$R'_1$ is a substituted or unsubstituted aryl, alkenyl, or alkyl. Generally, $R'_1$ is a substituted or unsubstituted C1-C12 alkyl. $R'_1$ is typically methyl or a C1-C12 alkyl that is optionally substituted with a reactive group.

$R'_3$, $R'_4$, $R_a$, $R_b$, $R_c$, and $R_d$ are independently —H, —F, —Cl, —Br, —I, —NO$_2$, —CN, —CO$_2$H, —SO$_3$H, —NHNH$_2$, —SH, alkoxylcarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxylamino, alkylthio, alkenyl, aryl, or alkyl. Alternatively, $R_c$ and $R_d$ in combination or $R'_3$ and $R'_4$ in combination can form a saturated or unsaturated 5- or 6-membered ring. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Generally, $R'_3$, $R'_4$, $R_a$, $R_b$, $R_c$ and $R_d$ are independently —H or unsubstituted alkyl groups. Typically, $R_a$ and $R_c$ are —H and $R'_3$, $R'_4$, $R_b$, and $R_d$ are —H or methyl.

c is an integer indicating the charge of the complex. Generally, c is an integer selected from −1 to −5 or +1 to +5 indicating a positive or negative charge. For a number of osmium complexes, c is +2 or +3.

X represents counter ion(s). Examples of suitable counter ions include anions, such as halide (e.g., fluoride, chloride, bromide or iodide), sulfate, phosphate, hexafluorophosphate, and tetrafluoroborate, and cations (in some embodiments, monovalent cations), such as lithium, sodium, potassium, tetralkylammonium, and ammonium. In an embodiment of an embodiment of the invention, X is a halide, such as chloride. The counter ions represented by X are not necessarily all the same.

d represents the number of counter ions and is typically from 1 to 5.

$L_1$, $L_2$, $L_3$ and $L_4$ are ligands attached to the transition metal via a coordinative bond. $L_1$, $L_2$, $L_3$ and $L_4$ can be monodentate ligands or, in any combination, bi-, ter-, or tetradentate ligands For example, $L_1$, $L_2$, $L_3$ and $L_4$ can combine to form two bidentate ligands such as, for example, two ligands selected from the group of substituted and unsubstituted 2,2'-biimidazoles, 2-(2-pyridyl)imidizoles, and 2,2'-bipyridines.

The term "alkyl" includes, for example, linear or branched, saturated aliphatic hydrocarbons. Examples of alkyl groups include methyl, ethyl, n-propyl, isopropyl, n-butyl, tert-butyl and the like. Unless otherwise noted, the term "alkyl" includes, for example, both alkyl and cycloalkyl groups.

The term "alkoxy" refers to, for example, an alkyl group joined to the remainder of the structure by an oxygen atom. Examples of alkoxy groups include methoxy, ethoxy, n-propoxy, isopropoxy, butoxy, tert-butoxy, and the like. In addition, unless otherwise noted, the term 'alkoxy' includes, for example, both alkoxy and cycloalkoxy groups.

The term "alkenyl" refers to, for example, an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl, and the like.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —NH$_2$, alkylamino, dialkylamino, trialkylammonium, alkanoylamino, arylcarboxamido, hydrazino, alkylthio, alkenyl, and reactive groups.

Examples of other $L_1$, $L_2$, $L_3$ and $L_4$ combinations of the transition metal complex include:

(A) $L_1$ is a monodentate ligand and $L_2$, $L_3$ and $L_4$ in combination form a terdentate ligand;

(B) $L_1$ and $L_2$ in combination are a bidentate ligand, and $L_3$ and $L_4$ are the same or different monodentate ligands;

(C) $L_1$ and $L_2$ in combination, and $L_3$ and $L_4$ in combination form two independent bidentate ligands which can be the same or different; and (D) $L_1$, $L_2$, $L_3$ and $L_4$ in combination form a tetradentate ligand.

Examples of suitable monodentate ligands include, but are not limited to, —F, —Cl, —Br, —I, —CN, —SCN, —OH, $H_2O$, $NH_3$, alkylamine, dialkylamine, trialkylamine, alkoxy or heterocyclic compounds. The alkyl or aryl portions of any of the ligands are optionally substituted by —F, —Cl, —Br, —I, alkylamino, dialkylamino, trialkylammonium (except on aryl portions), alkoxy, alkylthio, aryl, or a reactive group. Any alkyl portions of the monodentate ligands generally contain 1 to 12 carbons. More typically, the alkyl portions contain 1 to 6 carbons. In other embodiments, the monodentate ligands are heterocyclic compounds containing at least one nitrogen, oxygen, or sulfur atom. Examples of suitable heterocyclic monodentate ligands include imidazole, pyrazole, oxazole, thiazole, pyridine, pyrazine and derivatives thereof. Suitable heterocyclic monodentate ligands include substituted and unsubstituted imidazole and substituted and unsubstituted pyridine having the following general formulas 4 and 5, respectively:

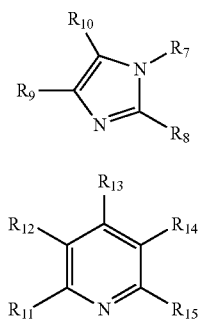

With regard to formula 4, $R_7$ is generally a substituted or unsubstituted alkyl, alkenyl, or aryl group. Typically, $R_7$ is a substituted or unsubstituted C1 to C12 alkyl or alkenyl. The substitution of inner coordination sphere chloride anions by imidazoles does not typically cause a large shift in the redox potential in the oxidizing direction, differing in this respect from substitution by pyridines, which typically results in a large shift in the redox potential in the oxidizing direction.

$R_8$, $R_9$ and $R_{10}$ are independently —H, —F, —Cl, —Br, —I, —$NO_2$, —CN, —$CO_2H$, —$SO_3H$, —$NHNH_2$, —SH, aryl, alkoxycarbonyl, alkylaminocarbonyl, dialkylaminocarbonyl, —OH, alkoxy, —$NH_2$, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_9$ and $R_{10}$, in combination, form a fused 5 or 6-membered ring that is saturated or unsaturated. The alkyl portions of the substituents generally contain 1 to 12 carbons and typically contain 1 to 6 carbon atoms. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. In some embodiments, $R_8$, $R_9$ and $R_{10}$ are —H or substituted or unsubstituted alkyl. In an embodiment of an embodiment of the invention, $R_8$, $R_9$ and $R_{10}$ are —H.

With regard to Formula 5, $R_{11}$, $R_{12}$, $R_{13}$, $R_{14}$ and $R_{15}$ are independently —H, —F, —Cl, —Br, —I, —$NO_2$, —CN, —$CO_2H$, alkoxycarbonyl, alkylaminocarbonyl, dialkylaminocarbonyl, —OH, alkoxy, —$NH_2$, alkylamino, dialkylamino, alkanoylamino, arylcarboxamido, hydrazino, alkylhydrazino, hydroxylamino, alkoxyamino, alkylthio, alkenyl, aryl, or alkyl. The alkyl or aryl portions of any of the substituents are optionally substituted by —F, —Cl, —Br, —I, alkylamino, dialkylamino, trialkylammonium (except for aryl portions), alkoxy, alkylthio, aryl, or a reactive group. Generally, $R_{11}$, $R_{12}$, $R_{13}$, $R_{14}$ and $R_{15}$ are —H, methyl, C1-C2 alkoxy, C1-C2 alkylamino, C2-C4 dialkylamino, or a C1-C6 lower alkyl substituted with a reactive group.

One example includes $R_{11}$ and $R_{15}$ as —H, $R_{12}$ and $R_{14}$ as the same and —H or methyl, and $R_{13}$ as —H, C1 to C12 alkoxy, —$NH_2$, C1 to C12 alkylamino, C2 to C24 dialkylamino, hydrazino, C1 to C12 alkylhydrazino, hydroxylamino, C1 to C12 alkoxyamino, C1 to C12 alkylthio, or C1 to C12 alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

A "reactive group" is a functional group of a molecule that is capable of reacting with another compound to couple at least a portion of that other compound to the molecule. Exemplary reactive groups include, but are not limited to, carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodiimides.

Examples of suitable bidentate ligands include, but are not limited to, amino acids, oxalic acid, acetylacetone, diaminoalkanes, ortho-diaminoarenes, 2,2'-biimidazole, 2,2'-bioxazole, 2,2'-bithiazole, 2-(2-pyridyl)imidazole, and 2,2'-bipyridine and derivatives thereof. Particularly suitable bidentate ligands for redox mediators include substituted and unsubstituted 2,2'-biimidazole, 2-(2-pyridyl)imidazole and 2,2'-bipyridine. The substituted 2,2' biimidazole and 2-(2-pyridyl)imidazole ligands can have the same substitution patterns described above for the other 2,2'-biimidazole and 2-(2-pyridyl)imidazole ligand. A 2,2'-bipyridine ligand has the following general formula 6:

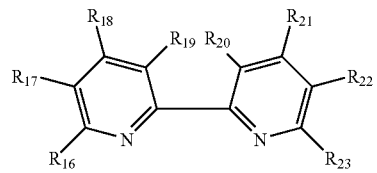

$R_{16}$, $R_{17}$, $R_{18}$, $R_{19}$, $R_{20}$, $R_{21}$, $R_{22}$ and $R_{23}$ are independently —H, —F, —Cl, —Br, —I, —$NO_2$, —CN, —$CO_2H$, —$SO_3H$, —$NHNH_2$, —SH, aryl, alkoxycarbonyl, alkylaminocarbonyl, dialkylaminocarbonyl, —OH, alkoxy, —$NH_2$, alkylamino, dialkylamino, alkanoylamino, arylcarboxamido, hydrazino, alkylhydrazino, hydroxylamino, alkoxylamino, alkylthio, alkenyl, or alkyl. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Specific examples of suitable combinations of $R_{16}$, $R_{17}$, $R_{18}$, $R_{19}$, $R_{20}$, $R_{21}$, $R_{22}$ and $R_{23}$ include $R_{16}$ and $R_{23}$ as H or methyl; $R_{17}$ and $R_{22}$ as the same and —H or methyl; and $R_{19}$ and $R_{20}$ as the same and —H or methyl. An alternative combination is where one or more adjacent pairs of substituents $R_{16}$ and $R_{17}$, on the one hand, and $R_{22}$ and $R_{23}$, on the other hand, independently form a saturated or unsaturated 5- or 6-membered ring. Another combination includes $R_{19}$ and $R_{20}$ forming a saturated or unsaturated five or six membered ring.

Another combination includes $R_{16}$, $R_{17}$, $R_{19}$, $R_{20}$, $R_{22}$ and $R_{23}$ as the same and —H and $R_{18}$ and $R_{21}$ as independently —H, alkoxy, —NH$_2$, alkylamino, dialkylamino, alkylthio, alkenyl, or alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. As an example, $R_{18}$ and $R_{21}$ can be the same or different and are —H, C1-C6 alkyl, C1-C6 amino, C1 to C12 alkylamino, C2 to C12 dialkylamino, C1 to C12 alkylthio, or C1 to C12 alkoxy, the alkyl portions of any of the substituents are optionally substituted by a —F, —Cl, —Br, —I, aryl, C2 to C12 dialkylamino, C3 to C18 trialkylammonium, C1 to C6 alkoxy, C1 to C6 alkylthio or a reactive group.

Examples of suitable terdentate ligands include, but are not limited to, diethylenetriamine, 2,2',2"-terpyridine, 2,6-bis(N-pyrazolyl)pyridine, and derivatives of these compounds. 2,2', 2"-terpyridine and 2,6-bis(N-pyrazolyl)pyridine have the following general formulas 7 and 8 respectively:

bonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxylamino, alkylthio, alkenyl, aryl, or alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Typically, the alkyl and alkoxy groups are C1 to C12 and, in some embodiments, $R_{27}$ and $R_{29}$ are the same and are —H.

Examples of suitable tetradentate ligands include, but are not limited to, triethylenetriamine, ethylenediaminediacetic acid, tetraaza macrocycles and similar compounds as well as derivatives thereof.

Examples of suitable transition metal complexes are illustrated using Formula 9 and 10:

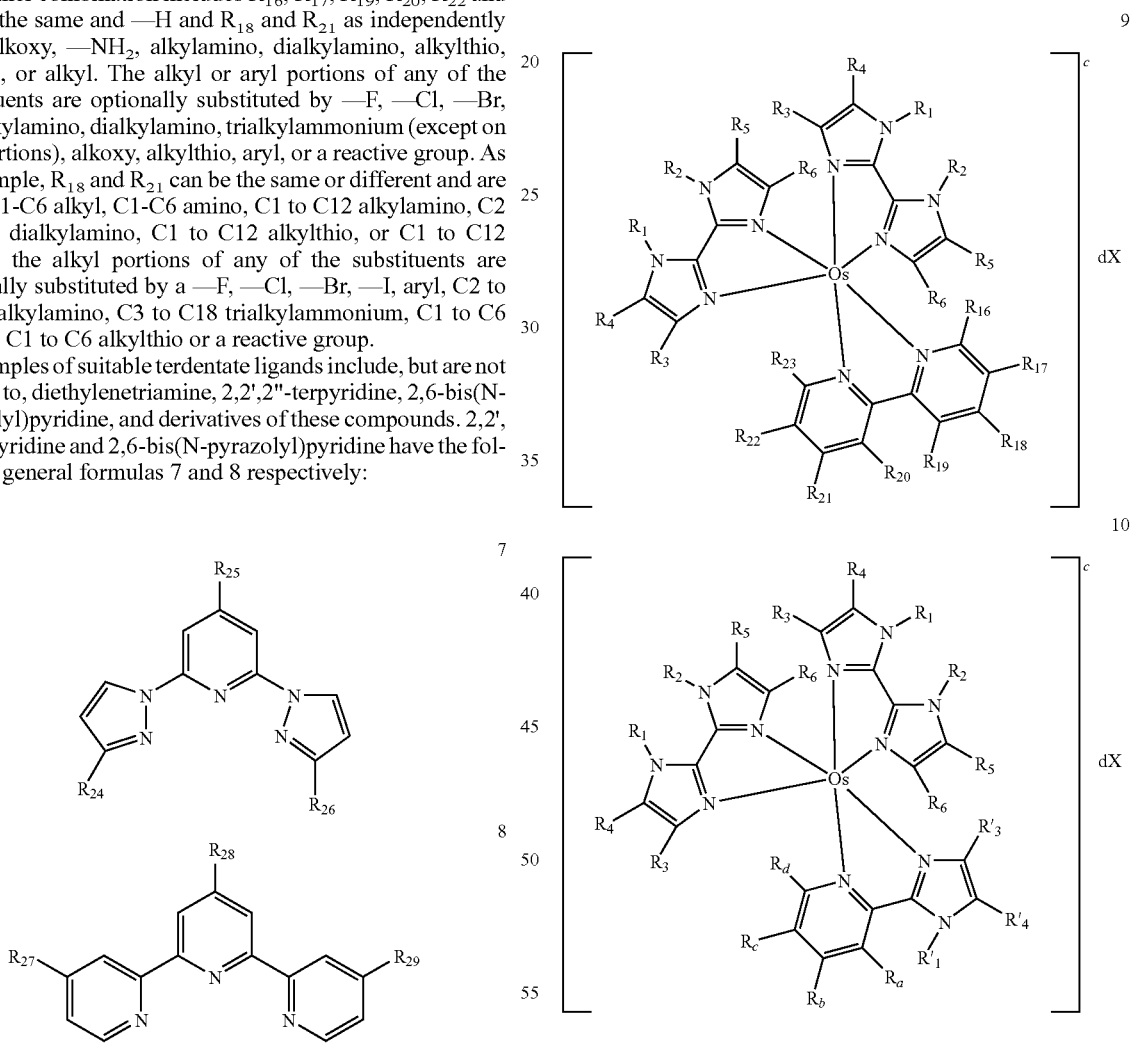

With regard to transition metal complexes of formula 9, the metal osmium is complexed to two substituted 2,2'-biimidazole ligands and one substituted or unsubstituted 2,2'-bipyridine ligand. $R_1$, $R_2$, $R_3$, $R_4$, $R_5$, $R_6$, $R_{16}$, $R_{17}$, $R_{18}$, $R_{19}$, $R_{20}$, $R_{21}$, $R_{22}$, $R_{23}$, c, d, and X are the same as described above.

In one embodiment, $R_1$ and $R_2$ are methyl; $R_3$, $R_4$, $R_5$, $R_6$, $R_{16}$, $R_{17}$, $R_{19}$, $R_{20}$, $R_{22}$ and $R_{23}$ are —H; and $R_{18}$ and $R_{21}$ are the same and are —H, methyl, or methoxy. In an embodiment of an embodiment of the invention, $R_{18}$ and $R_{21}$ are methyl or methoxy.

With regard to formula 7, $R_{24}$, $R_{25}$ and $R_{26}$ are independently —H or substituted or unsubstituted C1 to C12 alkyl. Typically, $R_{24}$, $R_{25}$ and $R_{26}$ are —H or methyl and, in some embodiments, $R_{24}$ and $R_{26}$ are the same and are —H. Other substituents at these or other positions of the compounds of formulas 7 and 8 can be added.

With regard to formula 8, $R_{27}$, $R_{28}$ and $R_{29}$ are independently —H, —F, —Cl, —Br, —I, —NO$_2$, —CN, —CO$_2$H, —SO$_3$H, —NHNH$_2$, —SH, alkoxycarbonyl, alkylaminocar- In another embodiment, $R_1$ and $R_2$ are methyl; $R_3$, $R_4$, $R_5$, $R_6$, $R_{16}$, $R_{17}$, $R_{18}$, $R_{19}$, $R_{20}$, $R_{22}$ and $R_{23}$ are —H; and $R_{21}$ is halo, C1 to C12 alkoxy, C1 to C12 alkylamino, or C2 to C24 dialkylamino. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. For example, $R_{21}$ is a C1 to C12 alkylamino or C2 to C24 dialkylamino, the alkyl portion(s) of which are substituted with a reactive group, such as a carboxylic acid, activated ester, or amine. Typically, the alkylamino group has 1 to 6 carbon atoms and the dialkylamino group has 2 to 8 carbon atoms.

With regard to transition metal complexes of formula 10, the metal osmium is complexed to two substituted 2,2'-biimidazole ligands and one substituted or unsubstituted 2-(2-pyridyl)imidazole ligand. $R_1$, $R_2$, $R_3$, $R_4$, $R_5$, $R_6$, $R'_1$, $R'_3$, $R'_4$, $R_a$, $R_b$, $R_c$, $R_d$, c, d, and X are the same as described above.

In one embodiment, $R_1$ and $R_2$ are methyl; $R_3$, $R_4$, $R_5$, $R_6$, $R'_3$, $R'_4$ and $R_d$ are independently —H or methyl; $R_a$ and $R_c$ are the same and are —H; and $R_b$ is C1 to C12 alkoxy, C1 to C12 alkylamino, or C2 to C24 dialkylamino. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

A list of specific examples of preferred transition metal complexes with respective redox potentials is shown in Table 1.

TABLE 1

Redox Potentials of Selected Transition Metal Complexes

| Complex | Structure | $E_{1/2}$ (vs Ag/AgCl)/mV* |
|---|---|---|
| I | 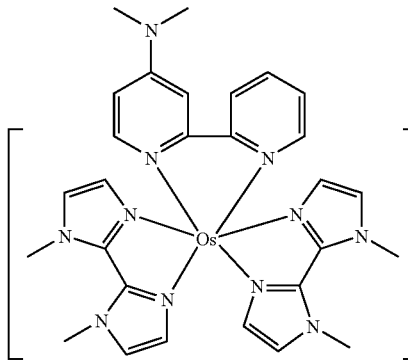 [Os(1,1'-dimethyl-2,2'-biimidazole)$_2$(4-dimethylamino-2,2'-bipyridine)]Cl$_3$ | −110 |
| II | 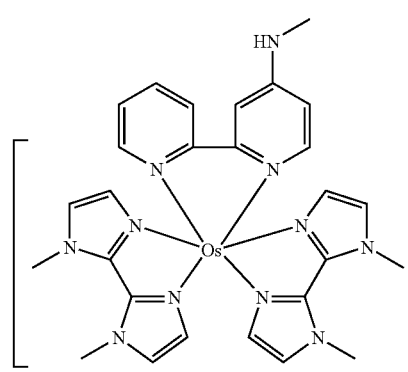 [Os(1,1'-dimethyl-2,2'-biimidazole)$_2$(4-methylamino-2,2'-bipyridine)]Cl$_3$ | −100 |

TABLE 1-continued

Redox Potentials of Selected Transition Metal Complexes

| Complex | Structure | $E_{1/2}$ (vs Ag/AgCl)/mV* |
|---|---|---|
| III | [Os(1,1'-dimethyl-2,2'-biimidazole)$_2$(4-bromo-2,2'-bipyridine)]Cl$_3$ | 128 |
| IV | [Os(1,1'-dimethyl-2,2'-biimidazole)$_2$(4-di(2-methoxyethyl)amino-2,2'-bipyridine)]Cl$_3$ | −86 |
| V | [Os(1,1'-dimethyl-2,2'-biimidazole)$_2$(4-(3-methoxypropyl)amino-2,2'-bipyridine)]Cl$_3$ | −97 |

TABLE 1-continued

Redox Potentials of Selected Transition Metal Complexes

| Complex | Structure | $E_{1/2}$ (vs Ag/AgCl)/mV* |
|---|---|---|
| VI | [Os(1,1'-dimethyl-2,2'-biimidazole)$_2$(4-diethylamino-2,2'-bipyridine)]Cl$_3$ | −120 |
| VII | [Os(1,1'-dimethyl-2,2'-biimidazole)$_2$(4,4'-dimethyl-2,2'-bipyridine)]Cl$_3$ | 32 |
| VIII | [Os(1,1'-dimethyl-2,2'-biimidazole)$_2$(4-(6-hydroxyhexyl)amino-2,2'-bipyridine)]Cl$_3$ | −100 |

TABLE 1-continued
Redox Potentials of Selected Transition Metal Complexes
| Complex | Structure | $E_{1/2}$ (vs Ag/AgCl)/mV* |
|---|---|---|
| IX | 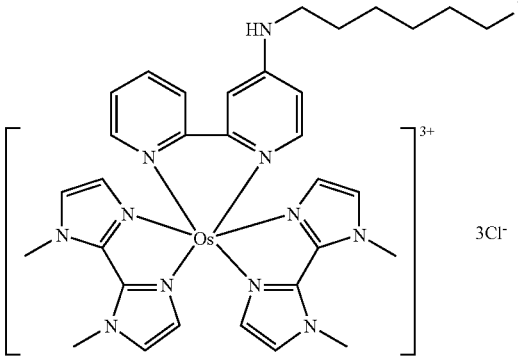 [Os(1,1'-dimethyl-2,2'-biimidazole)$_2$(4-(6-aminohexyl)amino-2,2'-bipyridine)]Cl$_3$ | −93 |
| X | 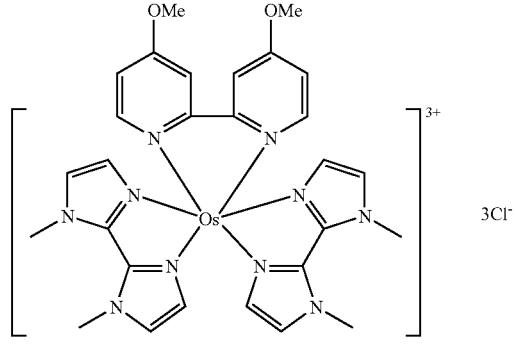 [Os(1,1'-dimethyl-2,2'-biimidazole)$_2$(4-methoxypyridine)$_2$]Cl$_3$ | −125 |
| XI | 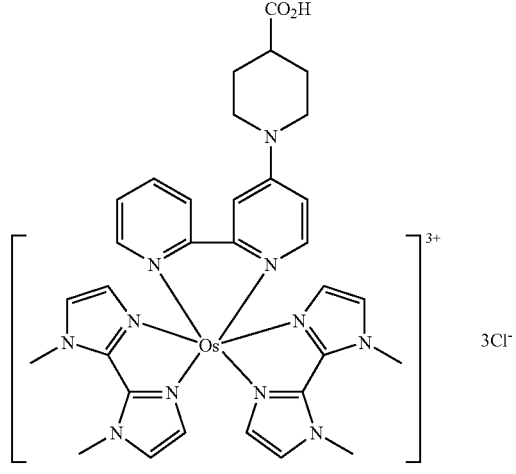 [Os(1,1'-dimethyl-2,2'-biimidazole)$_2$(4-(N-(4-carboxy)piperidino)-2,2'-bipyridine)]Cl$_3$ | −60 |

TABLE 1-continued

Redox Potentials of Selected Transition Metal Complexes

| Complex | Structure | $E_{1/2}$ (vs Ag/AgCl)/mV* |
|---|---|---|
| XII | [Os(1,1'-dimethyl-2,2'-biimidazole)$_2$(1-methyl-2-(2-pyridyl)imidazole)]Cl$_3$ | −74 |
| XIII | [Os(1,1'-dimethyl-2,2'-biimidazole)$_2$(1-methyl-2-(6-methylpyrid-2-yl)imidazole)]Cl$_3$ | −97 |
| IVX | [Os(1,1'-dimethyl-2,2'-biimidazole)$_2$(1-(6-aminohexyl)-2-(6-methylpyrid-2-yl)imidazole)]Cl$_3$ | −81 |

TABLE 1-continued

Redox Potentials of Selected Transition Metal Complexes

| Complex | Structure | $E_{1/2}$ (vs Ag/AgCl)/mV* |
|---|---|---|
| VX | 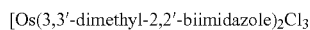 [Os(3,3'-dimethyl-2,2'-biimidazole)₂Cl₃ | −230 |

*Redox potentials were estimated by averaging the positions of the reduction wave peaks and the oxidation wave peaks of cyclic voltammograms (CVs) obtained in pH 7 PBS buffer with a glassy carbon working electrode, a graphite counter electrode and a standard Ag/AgCl reference electrode at a sweep rate of 50 mV/s.

The transition metal complexes of Formula I also include transition metal complexes that are coupled to a polymeric backbone through one or more of L, $L_1$, $L_2$, $L_3$, and $L_4$. Additional examples of suitable transition metal complexes are described in U.S. patent application Ser. No. 09/712,065, entitled "Polymeric Transition Metal Complexes and Uses Thereof", incorporated herein by reference. In some embodiments, the polymeric backbone has functional groups that act as ligands of the transitional metal complex. Such polymeric backbones include, for example, poly(4-vinylpyridine) and poly(N-vinylimidazole) in which the pyridine and imidazole groups, respectively, can act as monodentate ligands of the transition metal complex.

The polymeric backbone has the following general formula, where n may be 2, n' may be 17, and n" may be 1:

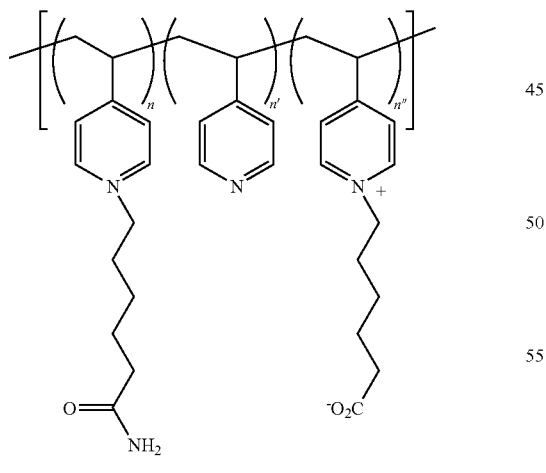

In other embodiments, the transition metal complex of the redox polymers of an embodiment of the invention can be the reaction product between a reactive group on a precursor polymer and a reactive group on a ligand of a precursor transition metal complex (such as a complex of Formula 1 where one of L, $L_1$, $L_2$, $L_3$ and $L_4$ includes a reactive group as described above). Suitable precursor polymers include, for example, poly(acrylic acid) (Formula 11), styrene/maleic anhydride copolymer (Formula 12), methylvinylether/maleic anhydride copolymer (GANTREX polymer) (Formula 13), poly(vinylbenzylchloride) (Formula 14), poly(allylamine) (Formula 15), polylysine (Formula 16), carboxy-poly(vinylpyridine) (Formula 17), and poly(sodium 4-styrene sulfonate) (Formula 18).

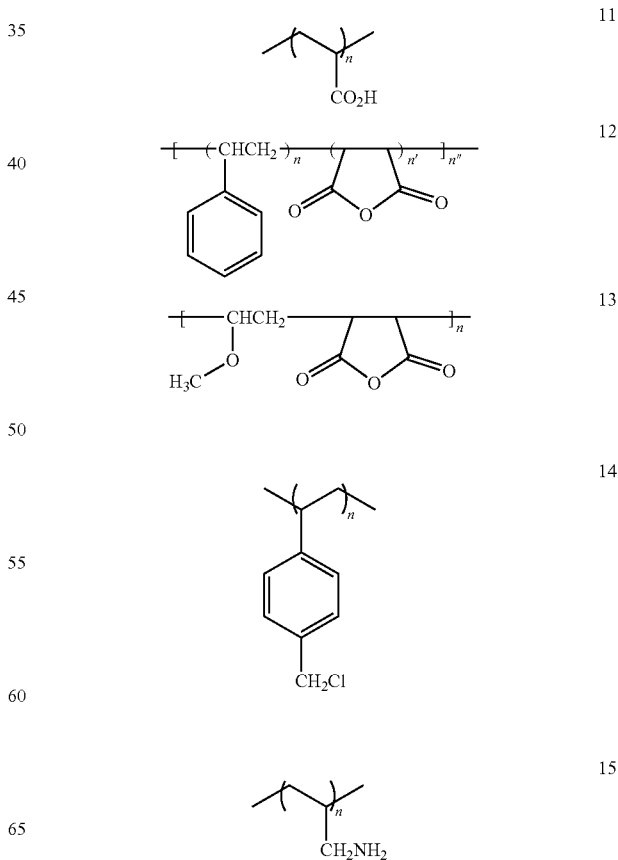

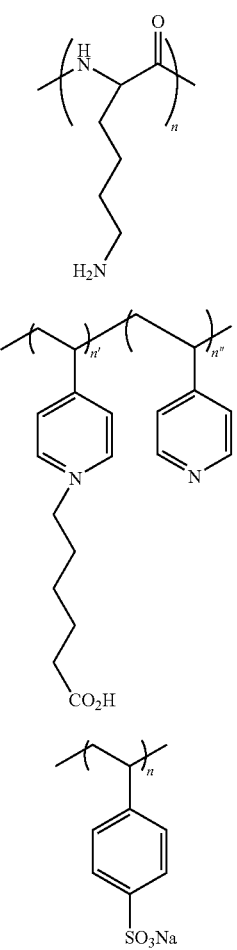

Alternatively, the transition metal complex can have reactive group(s) for immobilization or conjugation of the complexes to other substrates or carriers, examples of which include, but are not limited to, macromolecules (e.g., enzymes) and surfaces (e.g., electrode surfaces).

For reactive attachment to polymers, substrates, or other carriers, the transition metal complex precursor includes at least one reactive group that reacts with a reactive group on the polymer, substrate, or carrier. Typically, covalent bonds are formed between the two reactive groups to generate a linkage. Examples of such linkages are provided in Table 2, below. Generally, one of the reactive groups is an electrophile and the other reactive group is a nucleophile.

TABLE 2

Examples of Reactive Group Linkages

| First Reactive Group | Second Reactive Group | Resulting Linkage |
| --- | --- | --- |
| Activated ester* | Amine | Carboxamide |
| Acrylamide | Thiol | Thioether |
| Acyl azide | Amine | Carboxamide |
| Acyl halide | Amine | Carboxamide |
| Carboxylic acid | Amine | Carboxamide |
| Aldehyde or ketone | Hydrazine | Hydrazone |
| Aldehyde or ketone | Hydroxyamine | Oxime |
| Alkyl halide | Amine | Alkylamine |
| Alkyl halide | Carboxylic acid | Carboxylic ester |
| Alkyl halide | Imidazole | Imidazolium |

TABLE 2-continued

Examples of Reactive Group Linkages

| First Reactive Group | Second Reactive Group | Resulting Linkage |
| --- | --- | --- |
| Alkyl halide | Pyridine | Pyridinium |
| Alkyl halide | Alcohol/phenol | Ether |
| Alkyl halide | Thiol | Thioether |
| Alkyl sulfonate | Thiol | Thioether |
| Alkyl sulfonate | Pyridine | Pyridinium |
| Alkyl sulfonate | Imidazole | Imidazolium |
| Alkyl sulfonate | Alcohol/phenol | Ether |
| Anhydride | Alcohol/phenol | Ester |
| Anhydride | Amine | Carboxamide |
| Aziridine | Thiol | Thioether |
| Aziridine | Amine | Alkylamine |
| Aziridine | Pyridine | Pyridinium |
| Epoxide | Thiol | Thioether |
| Epoxide | Amine | Alkylamine |
| Epoxide | Pyridine | Pyridinium |
| Halotriazine | Amine | Aminotriazine |
| Halotriazine | Alcohol | Triazinyl ether |
| Imido ester | Amine | Amidine |
| Isocyanate | Amine | Urea |
| Isocyanate | Alcohol | Urethane |
| Isothiocyanate | Amine | Thiourea |
| Maleimide | Thiol | Thioether |
| Sulfonyl halide | Amine | Sulfonamide |

*Activated esters, as understood in the art, generally include esters of succinimidyl, benzotriazolyl, or aryl substituted by electron-withdrawing groups such as sulfo, nitro, cyano, or halo; or carboxylic acids activated by carbodiimides.

Transition metal complexes used in the redox polymers of embodiments of an embodiment of the invention can be soluble in water or other aqueous solutions, or in organic solvents. In general, transition metal complexes can be made soluble in either aqueous or organic solvents by having an appropriate counter ion or ions, X. For example, transition metal complexes with small counter anions, such as $F^-$, $Cl^-$, and $Br^-$, tend to be water soluble. On the other hand, transition metal complexes with bulky counter anions, such as $I^-$, $BF_4^-$ and $PF_6^-$, tend to be soluble in organic solvents. In an embodiment of an embodiment of the invention, the solubility of transition metal complexes of aspects of an embodiment of the invention is greater than about 0.1 M (moles/liter) at 25° C. for a desired solvent.

The use of transition metal complexes as redox mediators is described, for example, in U.S. Pat. Nos. 5,262,035; 5,262,305; 5,320,725; 5,365,786; 5,593,852; 5,665,222; 5,972,199; and 6,143,164 and U.S. patent application Ser. Nos. 09/034,372, (now U.S. Pat. No. 6,134,461); Ser. No. 09/070,677, (now U.S. Pat. No. 6,175,752); Ser. No. 09/295,962, (now U.S. Pat. No. 6,338,790) and Ser. No. 09/434,026, all of which are herein incorporated by reference. The transitional metal complexes described herein can typically be used in place of those discussed in the references listed above.

Redox Polymers

Suitable redox polymers for use with the electrochemical analyte sensors may comprise, inter alia, a transition metal complex, a cross-linker and a polymeric backbone. Such redox polymers are useful as redox mediators in electrochemical biosensors for the detection of analytes in biofluids, for example. In some aspects the redox polymers may include coordination complexes including an osmium.

In general, the redox polymer is disposed on or in proximity to (e.g., in a solution surrounding) a working electrode. The redox polymer transfers electrons between the working electrode and an analyte. In some preferred embodiments, an enzyme is also included to facilitate the transfer. For example, the redox polymer transfers electrons between the working electrode and glucose (typically via an enzyme) in an enzyme-catalyzed reaction of glucose. Redox polymers are particularly useful for forming non-leachable coatings on the working electrode. These can be formed, for example, by crosslinking the redox polymer on the working electrode, or by cross-linking the redox polymer and the enzyme on the working electrode.

Transition metal complexes can enable accurate, reproducible and quick or continuous assays. Transition metal complex redox mediators accept electrons from, or transfer electrons to, enzymes or analytes at a high rate and also exchange electrons rapidly with an electrode. Typically, the rate of self exchange, the process in which a reduced redox mediator transfers an electron to an oxidized redox mediator, is rapid. At a defined redox mediator concentration, this provides for more rapid transport of electrons between the enzyme (or analyte) and electrode, and thereby shortens the response time of the sensor. Additionally, the transition metal complex redox mediators disclosed herein are typically stable under ambient light and at the temperatures encountered in use, storage and transportation. In an embodiment of an embodiment of the invention, the transition metal complex redox mediators do not undergo chemical change, other than oxidation and reduction, in the period of use or under the conditions of storage, though the redox mediators can be designed to be activated by reacting, for example, with water or the analyte.

A transition metal complex can be used as a redox mediator in combination with a redox enzyme to electrooxidize or electroreduce the analyte or a compound derived of the analyte, for example by hydrolysis of the analyte. The redox potentials of the redox mediators are generally more positive (i.e. more oxidizing) than the redox potentials of the redox enzymes when the analyte is electrooxidized and more negative when the analyte is electroreduced. For example, the redox potentials of the preferred transition metal complex redox mediators used for electrooxidizing glucose with an analyte response dehydrogenase optionally complexed with a co-factor, such as GDH optionally complexed with a co-factor such as FAD, is between about −200 mV and +200 mV versus a Ag/AgCl reference electrode, and the most preferred mediators have redox potentials between about −100 mV and about +100 mV versus a Ag/AgCl reference electrode.

Crosslinked Transition Metal Complex Polymers

Electron transport involves an exchange of electrons between segments of the redox polymers (e.g., one or more transition metal complexes coupled to a polymeric backbone, as described above) in a crosslinked film disposed on an electrode. A transition metal complex can be bound to the polymer backbone though covalent, coordinative or ionic bonds, where covalent and coordinative binding are preferred. Electron exchange occurs, for example, through the collision of different segments of the crosslinked redox polymer. Electrons transported through the redox polymer can originate from, for example, electrooxidation or electroreduction of an enzymatic substrate, such as, for example, the oxidation of glucose by an analyte response dehydrogenase optionally complexed with a co-factor, such as glucose dehydrogenase.

The degree of crosslinking of the redox polymer can influence the transport of electrons or ions and thereby the rates of the electrochemical reactions. Excessive crosslinking of the polymer can reduce the mobility of the segments of the redox polymer. A reduction in segment mobility can slow the diffusion of electrons or ions through the redox polymer film. A reduction in the diffusivity of electrons, for example, can require a concomitant reduction in the thickness of the film on the electrode where electrons or electron vacancies are collected or delivered. The degree of crosslinking in a redox polymer film can thus affect the transport of electrons from, for example, an enzyme to the transition metal redox centers of the redox polymer such as, for example, $Os^{2+/3+}$ metal redox centers; between redox centers of the redox polymer; and from these transition metal redox centers to the electrode.

Inadequate crosslinking of a redox polymer can result in excessive swelling of the redox polymer film and to the leaching of the components of the redox polymer film. Excessive swelling can also result in the migration of the swollen polymer into the analyzed solution, in the softening of the redox polymer film, in the film's susceptibility to removal by shear, or any combination of these effects.

Crosslinking can decrease the leaching of film components and can improve the mechanical stability of the film under shear stress. For example, as disclosed in Binyamin, G. and Heller, A; *Stabilization of Wired Glucose Oxidase Anodes Rotating at* 1000 *rpm at* 37° C.; Journal of the Electrochemical Society, 146(8), 2965-2967, 1999, herein incorporated by reference, replacing a difunctional cross-linker, such as polyethylene glycol diglycidyl ether, with a trifunctional cross-linker such as N,N-diglycidyl-4-glycidyloxyaniline, for example, can reduce leaching and shear problems associated with inadequate crosslinking.

Examples of other bifunctional, trifunctional and tetrafunctional cross-linkers are listed below:

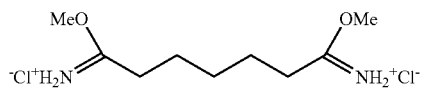

Amine-reactive Bifunctional Crosslinkers

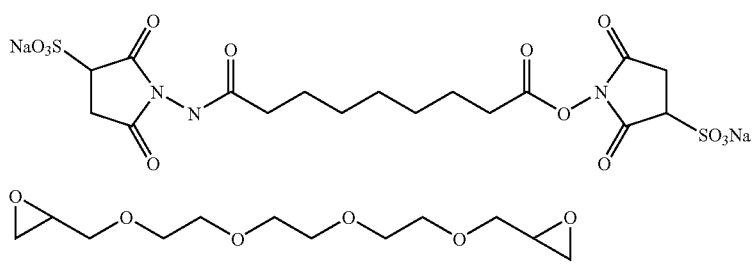

Pyridine- or Imidazole-reactive Bifunctional Crosslinkers

-continued

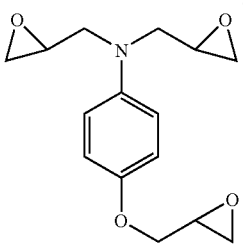

Pyridine- or Imidazole-reactive trifunctional Crosslinker

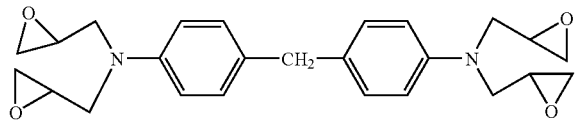

Pyridine- or Imidazole-reactive Tetrafunctional Crosslinkers

Alternatively, the number of crosslinking sites can be increased by reducing the number of transition metal complexes attached to the polymeric backbone, thus making more polymer pendant groups available for crosslinking. One important advantage of at least some of the redox polymers is the increased mobility of the pendant transition metal complexes, resulting from the flexibility of the pendant groups. As a result, in at least some embodiments, fewer transition metal complexes per polymer backbone are needed to achieve a desired level of diffusivity of electrons and current density of analyte electrooxidation or electroreduction.

Coordination in Transition Metal Complex Polymers

Transition metal complexes can be directly or indirectly attached to a polymeric backbone, depending on the availability and nature of the reactive groups on the complex and the polymeric backbone. For example, the pyridine groups in poly(4-vinylpyridine) or the imidazole groups in poly(N-vinylimidazole) are capable of acting as monodentate ligands and thus can be attached to a metal center directly. Alternatively, the pyridine groups in poly(4-vinylpyridine) or the imidazole groups in poly(N-vinylimidazole) can be quaternized with a substituted alkyl moiety having a suitable reactive group, such as a carboxylate function, that can be activated to form a covalent bond with a reactive group, such as an amine, of the transition metal complex. (See Table 2 for a list of other examples of reactive groups).

Redox centers such as, for example, $Os^{2+/3+}$ can be coordinated with five heterocyclic nitrogens and an additional ligand such as, for example, a chloride anion. An example of such a coordination complex includes two bipyridine ligands which form stable coordinative bonds, the pyridine of poly(4-vinylpyridine) which forms a weaker coordinative bond, and a chloride anion which forms the least stable coordinative bond.

Alternatively, redox centers, such as $Os^{2+/3+}$, can be coordinated with six heterocyclic nitrogen atoms in its inner coordination sphere. In an embodiment of an embodiment of the invention the six coordinating atoms are paired in the ligands, for example, each ligand is composed of at least two rings. Pairing of the coordinating atoms can influence the potential of an electrode used in conjunction with redox polymers of embodiments of an embodiment of the invention.

Typically, for analysis of glucose, the potential at which the working electrode, coated with the redox polymer, is poised is negative of about +250 mV vs. SCE (standard calomel electrode). In an embodiment of an embodiment of the invention, the electrode is poised negative of about +150 mV vs. SCE. Poising the electrode at these potentials reduces the interfering electrooxidation of constituents of biological solutions such as, for example, urate, ascorbate and acetaminophen. The potential can be modified by altering the ligand structure of the complex.

The redox potential of a redox polymer, as described herein, is related to the potential at which the electrode is poised. Selection of a redox polymer with a desired redox potential allows tuning of the potential at which the electrode is best poised. The redox potentials of a number of the redox polymers described herein are negative of about +150 mV vs. SCE and can be negative of about +50 mV vs. SCE to allow the poising of the electrode potentials negative of about +250 mV vs. SCE and in an embodiment of an embodiment of the invention negative of about +150 mV vs. SCE.

The strength of the coordination bond can influence the potential of the redox centers in the redox polymers. Typically, the stronger the coordinative bond, the more positive the redox potential. A shift in the potential of a redox center resulting from a change in the coordination sphere of the transition metal can produce a labile transition metal complex. For example, when the redox potential of an $Os^{2+/3+}$ complex is downshifted by changing the coordination sphere, the complex becomes labile. Such a labile transition metal complex may be undesirable when fashioning a metal complex polymer for use as a redox mediator and can be avoided through the use of weakly coordinating multidentate or chelating heterocyclics as ligands.

Electrode Interference

Transition metal complexes used as redox mediators in electrodes can be affected by the presence of transition metals in the analyzed sample including, for example, $Fe^{3+}$ or $Zn^{2+}$. The addition of a transition metal cation to a buffer used to test an electrode results in a decline in the current produced. The degree of current decline depends on the presence of anions in the buffer which precipitate the transition metal cations. The lesser the residual concentration of transition metal cations in the sample solution, the more stable the current. Anions which aid in the precipitation of transition metal cations include, for example, phosphate. It has been found that a decline in current upon the addition of transition metal cations is most pronounced in non-phosphate buffers. If an electrode is transferred from a buffer containing a transition metal cation to a buffer substantially free of the transition metal cation, the original current is restored.

The decline in current is thought to be due to additional crosslinking of a pyridine-containing polymer backbone produced by the transition metal cations. The transition metal cations can coordinate nitrogen atoms of different chains and chain segments of the polymers. Coordinative crosslinking of nitrogen atoms of different chain segments by transition metal cations can reduce the diffusivity of electrons.

Serum and other physiological fluids contain traces of transition metal ions, which can diffuse into the films of electrodes made with the redox polymers of embodiments of an embodiment of the invention, lowering the diffusivity of electrons and thereby the highest current reached at high analyte concentration. In addition, transition metal ions like iron and copper can bind to proteins of enzymes and to the reaction centers or channels of enzymes, reducing their turnover rate. The resulting decrease in sensitivity can be remedied through the use of anions which complex with interfering transition metal ions, for example, in a buffer employed during the production of the transition metal complex. A non-cyclic polyphosphate such as, for example, pyrophosphate or triphosphate, can be used. For example, sodium or potassium non-cyclic polyphosphate buffers can be used to exchange phosphate anions for those anions in the transition metal complex which do not precipitate transition metal ions. The use of linear phosphates can alleviate the decrease in sensitivity by forming strong complexes with the damaging transition metal ions, assuring that their activity will be low. Other complexing agents can also be used as long as they are not electrooxidized or electroreduced at the potential at which the electrode is poised.

Electrochemical Sensors

Generally, embodiments of the invention relate to methods and devices for detecting at least one analyte, such as glucose, in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combineable devices, systems and methods and/or transferring data between an in vivo continuous system and a BG meter system.

An electrochemical sensor that includes the analyte-responsive dehydrogenase and optional co-factor can be formed on a substrate. The sensor may also include at least one counter electrode (or counter/reference electrode) and/or at least one reference electrode. An "electrochemical sensor" is a device configured to detect the presence and/or measure the level of an analyte in a sample, via an electrochemical oxidation or reduction reaction on the sensor, or via a sequence of chemical reactions where at least one of the chemical reactions is an electrochemical oxidation or reduction reactions on the sensor. These reactions are transduced to an electrical signal that can be correlated to an amount, concentration, or level of an analyte in the sample.

Accordingly, embodiments include analyte monitoring devices and systems that include an analyte sensor—at least a portion of which is positionable beneath the skin of the user— for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors described herein having an analyte-responsive dehydrogenase and optional co-factor may be configured for monitoring the level of the analyte over a time period which may range from minutes, hours, days, weeks, to months, or longer.

Of interest are analyte sensors, such as glucose sensors, having the analyte-responsive dehydrogenase and optional co-factor, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month or more. Future analyte levels may be predicted based on information obtained, e.g., the current analyte level at time to, the rate of change of the analyte, etc. Predictive alarms may notify the user of a predicted analyte levels that may be of concern in advance of the user's analyte level reaching the future level. This provides the user an opportunity to take corrective action.

FIG. 1 shows a data monitoring and management system such as, for example, an analyte (e.g., glucose) monitoring system 100 in accordance with certain embodiments. Embodiments of the subject invention are further described primarily with respect to glucose monitoring devices and systems, and methods of glucose detection, for convenience only and such description is in no way intended to limit the scope of the invention. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bidirectional communication. Further, the data processing unit 102 may include a transmitter or a transceiver to transmit and/or receive data to and/or from the primary receiver unit 104 and/or the data processing terminal 105 and/or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bidirectional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or a bi-directional communication device. A docking cradle may recharge a powers supply.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit may include a fixation element such as adhesive or the like to secure it to the user's body. A mount (not shown) attachable to the user and mateable with the unit 102 may be used. For example, a mount may include an adhesive surface. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In certain embodiments, the primary receiver unit 104 may include an analog interface section including and RF receiver and an antenna that is configured to communicate with the data processing unit 102 via the communication link 103, and a data processing section for processing the received data from the data processing unit 102 such as data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone™ or similar phone), mp3 player, pager, and the like), drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In certain embodiments, the data processing terminal 105, which may include an insulin pump, may be configured to receive the analyte signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1, may use one or more of: an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements), while avoiding potential data collision and interference.

Figure 2:
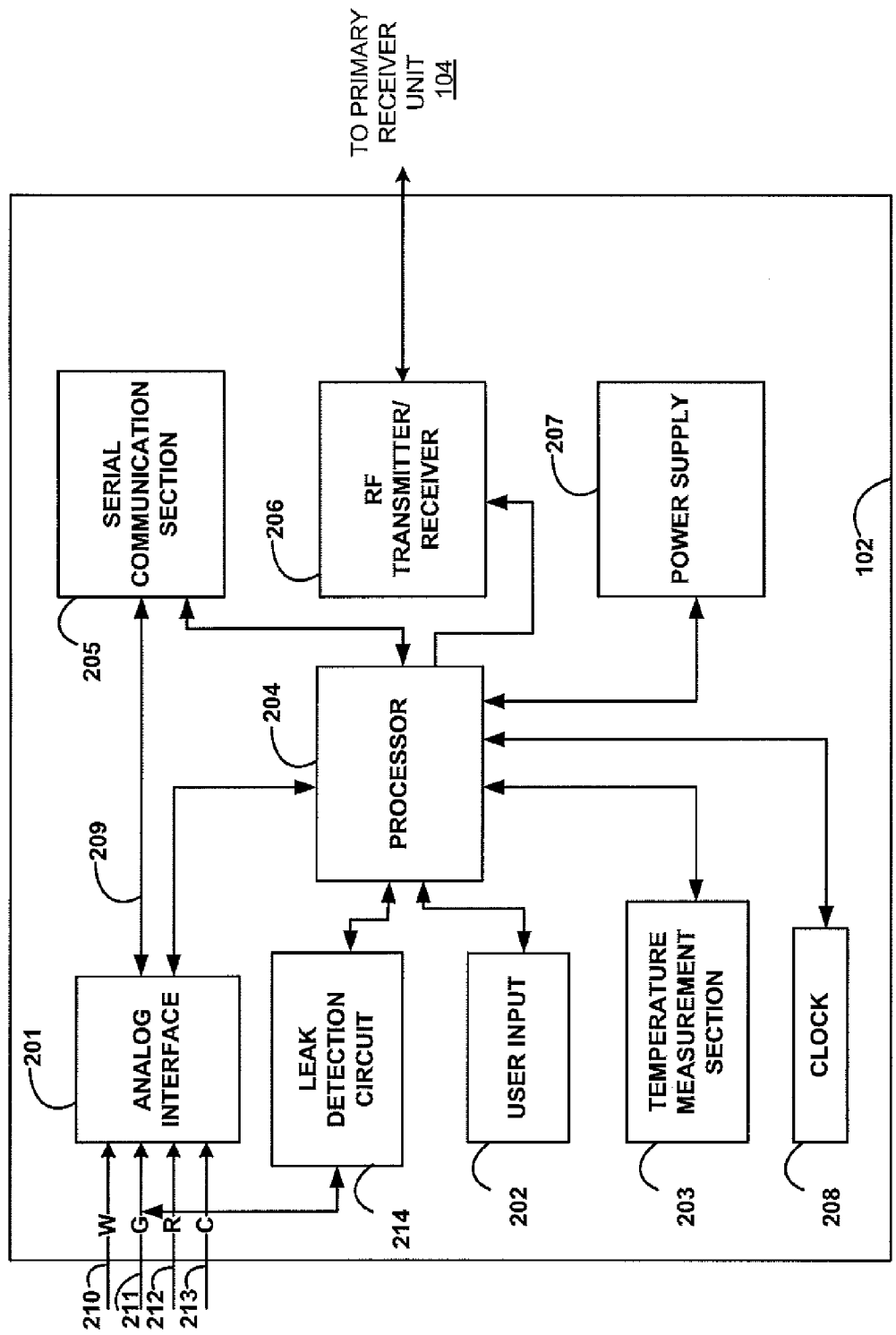
FIG. 2 shows a block diagram of an embodiment of the transmitter unit of the data monitoring and management system of FIG. 1.

FIG. 2 shows a block diagram of an embodiment of a data processing unit of the data monitoring and detection system shown in FIG. 1. User input and/or interface components may be included or a data processing unit may be free of user input and/or interface components. In certain embodiments, one or more application-specific integrated circuits (ASIC) may be used to implement one or more functions or routines associated with the operations of the data processing unit (and/or receiver unit) using for example one or more state machines and buffers.

As can be seen in the embodiment of FIG. 2, the sensor unit 101 (FIG. 1) includes four contacts, three of which are electrodes—work electrode (W) 210, reference electrode (R) 212, and counter electrode (C) 213, each operatively coupled to the analog interface 201 of the data processing unit 102. This embodiment also shows optional guard contact (G) 211. Fewer or greater electrodes may be employed. For example, the counter and reference electrode functions may be served by a single counter/reference electrode, there may be more than one working electrode and/or reference electrode and/or counter electrode, etc.

Figure 3:
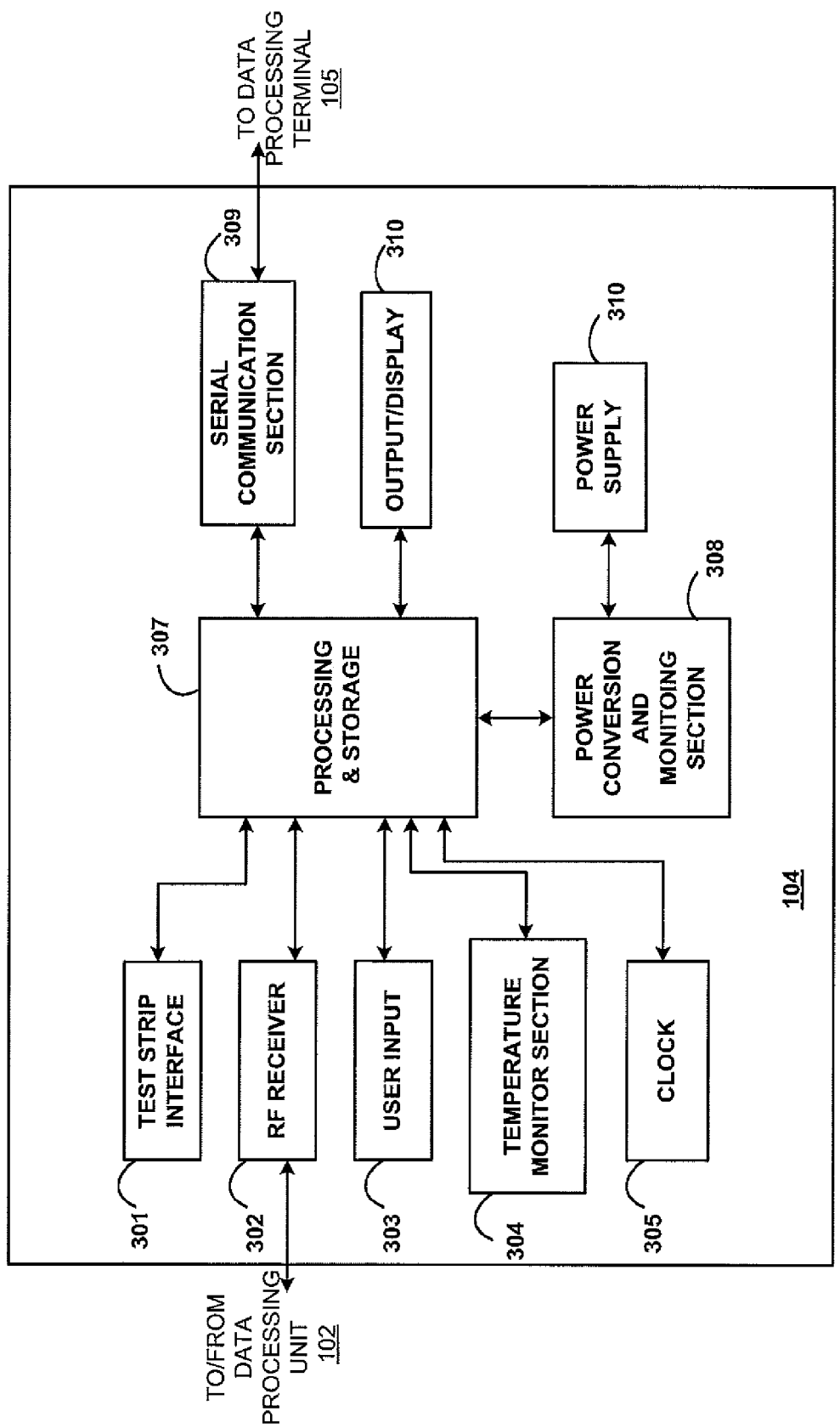
FIG. 3 shows a block diagram of an embodiment of the receiver/monitor unit of the data monitoring and management system of FIG. 1.

FIG. 3 is a block diagram of an embodiment of a receiver/monitor unit such as the primary receiver unit 104 of the data monitoring and management system shown in FIG. 1. The primary receiver unit 104 includes one or more of: a blood glucose test strip interface 301, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In certain embodiments, the test strip interface 301 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 310 of the primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® blood glucose test strips from Abbott Diabetes Care, Inc. Glucose information obtained by the in vitro glucose testing device may be used for a variety of purposes, computations, etc. For example, the information may be used to calibrate sensor 101, confirm results of the sensor 101 to increase the confidence thereof (e.g., in instances in which information obtained by sensor 101 is employed in therapy related decisions), etc.

In further embodiments, the data processing unit 102 and/or the primary receiver unit 104 and/or the secondary receiver unit 105, and/or the data processing terminal/infusion section 105 may be configured to receive the blood glucose value wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 105, or the data processing terminal/infusion section 105.

Additional detailed descriptions are provided in U.S. Pat. Nos. 5,262,035; 5,264,104; 5,262,305; 5,320,715; 5,593,852; 6,175,752; 6,650,471; 6,746,582, and in application Ser. No. 10/745,878 filed Dec. 26, 2003 entitled "Continuous Glucose Monitoring System and Methods of Use", each of which is incorporated herein by reference.

FIG. 4 schematically shows an embodiment of an analyte sensor in accordance with the embodiments of the invention. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include but are not limited to aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The sensor may be wholly implantable in a user or may be configured so that only a portion is positioned within (internal) a user and another portion outside (external) a user. For example, the sensor 400 may include a portion positionable above a surface of the skin 410, and a portion positioned below the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 5A shows a perspective view of an embodiment of an electrochemical analyte sensor 500 having a first portion (which in this embodiment may be characterized as a major portion) positionable above a surface of the skin 510, and a second portion (which in this embodiment may be characterized as a minor portion) that includes an insertion tip 530 positionable below the skin, e.g., penetrating through the skin and into, e.g., the subcutaneous space 520, in contact with the user's biofluid such as interstitial fluid. Contact portions of a working electrode 501, a reference electrode 502, and a counter electrode 503 are positioned on the portion of the sensor 500 situated above the skin surface 510. Working electrode 501, a reference electrode 502, and a counter electrode 503 are shown at the second section and particularly at the insertion tip 530. Traces may be provided from the electrode at the tip to the contact, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 501, 502 and 503, of the sensor 500 as well as the substrate and the dielectric layers are provided in a layered configuration or construction. For example, as shown in FIG. 5B, in one aspect, the sensor 500 (such as the sensor unit 101 FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing layer 508.

A first insulation layer such as a first dielectric layer 505 is disposed or layered on at least a portion of the first conducting layer 501, and further, a second conducting layer 509 may be disposed or stacked on top of at least a portion of the first insulation layer (or dielectric layer) 505. As shown in FIG. 5B, the second conducting layer 509 may provide the reference electrode 502, as described herein having an extended lifetime, which includes a layer of silver/silver chloride (Ag/AgCl).

A second insulation layer 506 such as a dielectric layer in one embodiment may be disposed or layered on at least a portion of the second conducting layer 509. Further, a third conducting layer 503 may provide the counter electrode 503. It may be disposed on at least a portion of the second insulation layer 506. Finally, a third insulation layer may be disposed or layered on at least a portion of the third conducting layer 503. In this manner, the sensor 500 may be layered such that at least a portion of each of the conducting layers is separated by a respective insulation layer (for example, a dielectric layer). The embodiment of FIGS. 5A and 5B show the layers having different lengths. Some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing there between and/or include dielectric material or insulation material disposed between the conducting layers/electrodes. Furthermore, in certain embodiments one or more of the electrodes 501, 502, 503 may be disposed on opposing sides of the substrate 504. In such embodiments, contact pads may be one the same or different sides of the substrate. For example, an electrode may be on a first side and its respective contact may be on a second side, e.g., a trace connecting the electrode and the contact may traverse through the substrate.

As noted above, analyte sensors may include an analyte-responsive enzyme to provide a sensing component or sensing layer. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analyte, such as oxygen, that can be directly electrooxidized or electroreduced on the working electrode. For these analytes, each working electrode includes a sensing layer (see for example sensing layer 408 of FIG. 5B) proximate to or on a surface of a working electrode. In many embodiments, a sensing layer is formed near or on only a small portion of at least a working electrode.

The sensing layer includes one or more components designed to facilitate the electrochemical oxidation or reduction of the analyte. The sensing layer may include, for example, a catalyst to catalyze a reaction of the analyte and produce a response at the working electrode, an electron transfer agent to transfer electrons between the analyte and the working electrode (or other component), or both.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes, e.g., over the counter electrode and/or reference electrode (or counter/reference is provided).

A sensing layer that is in direct contact with the working electrode may contain an electron transfer agent to transfer electrons directly or indirectly between the analyte and the working electrode, and/or a catalyst to facilitate a reaction of the analyte. For example, a glucose, lactate, or oxygen electrode may be formed having a sensing layer which contains a catalyst, such as glucose oxidase, lactate oxidase, or laccase, respectively, and an electron transfer agent that facilitates the electrooxidation of the glucose, lactate, or oxygen, respectively.

In other embodiments the sensing layer is not deposited directly on the working electrode. Instead, the sensing layer 64 may be spaced apart from the working electrode, and separated from the working electrode, e.g., by a separation layer. A separation layer may include one or more membranes or films or a physical distance. In addition to separating the working electrode from the sensing layer the separation layer may also act as a mass transport limiting layer and/or an interferent eliminating layer and/or a biocompatible layer.

In certain embodiments which include more than one working electrode, one or more of the working electrodes may not have a corresponding sensing layer, or may have a sensing layer which does not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing layers by, for example, subtracting the signal.

In certain embodiments, the sensing layer includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes such as ferrocene. Examples of inorganic redox species are hexacyanoferrate (III), ruthenium hexamine etc.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition.

An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, such as 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase or oligosaccharide dehydrogenase, flavine adenine dinucleotide (FAD) dependent glucose dehydrogenase, nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent (which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

Certain embodiments include a Wired Enzyme™ sensing layer (Abbott Diabetes Care) that works at a gentle oxidizing potential, e.g., a potential of about +40 mV vs. Ag/AgCl. This sensing layer uses an osmium (Os)-based mediator designed for low potential operation and is stably anchored in a polymeric layer. Accordingly, in certain embodiments the sensing element is redox active component that includes (1) Osmium-based mediator molecules attached by stable (bidente) ligands anchored to a polymeric backbone, and (2) glucose oxidase enzyme molecules. These two constituents are crosslinked together.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating, etc.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly (ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over an enzyme-containing sensing layer and allowing the solution to cure for about one to two days or other appropriate time period. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of these factors. A membrane applied in this manner may have any combination of the following functions: (1) mass transport limitation, i.e., reduction of the flux of analyte that can reach the sensing layer, (2) biocompatibility enhancement, or (3) interferent reduction.

In certain embodiments, the sensing system detects hydrogen peroxide to infer glucose levels. For example, a hydrogen peroxide-detecting sensor may be constructed in which a sensing layer includes enzyme such as glucose oxides, glucose dehydrogensae, or the like, and is positioned proximate to the working electrode. The sensing layer may be covered by one or more layers, e.g., a membrane that is selectively permeable to glucose. Once the glucose passes through the membrane, it is oxidized by the enzyme and reduced glucose oxidase can then be oxidized by reacting with molecular oxygen to produce hydrogen peroxide.

Certain embodiments include a hydrogen peroxide-detecting sensor constructed from a sensing layer prepared by crosslinking two components together, for example: (1) a redox compound such as a redox polymer containing pendent Os polypyridyl complexes with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. A glucose-sensing layer is constructed by crosslinking together (1) a redox polymer containing pendent Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In some embodiments, the substrate is flexible. For example, if the sensor is configured for implantation into a patient, then the sensor may be made flexible (although rigid sensors may also be used for implantable sensors) to reduce pain to the patient and damage to the tissue caused by the implantation of and/or the wearing of the sensor. A flexible substrate often increases the patient's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. One advantage of an implantable sensor having a rigid substrate is that the sensor may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the patient during operation of the sensor. However, the barb is typically small enough so that little damage is caused to the subcutaneous tissue when the sensor is removed for replacement.

An implantable sensor may also, optionally, have an anticlotting agent disposed on a portion the substrate which is implanted into a patient. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor that is to be implanted. The anticlotting agent may be applied, for example, by bath, spraying, brushing, or dipping. The anticlotting agent is allowed to dry on the sensor. The anticlotting agent may be immobilized on the surface of the sensor or it may be allowed to diffuse away from the sensor surface. Typically, the quantities of anticlotting agent disposed on the sensor are far below the amounts typically used for treatment of medical conditions involving blood clots and, therefore, have only a limited, localized effect.

Insertion Device

An insertion device can be used to subcutaneously insert the sensor into the patient. The insertion device is typically formed using structurally rigid materials, such as metal or rigid plastic. Preferred materials include stainless steel and ABS (acrylonitrile-butadiene-styrene) plastic. In some embodiments, the insertion device is pointed and/or sharp at the tip to facilitate penetration of the skin of the patient. A sharp, thin insertion device may reduce pain felt by the patient upon insertion of the sensor. In other embodiments, the tip of the insertion device has other shapes, including a blunt or flat shape. These embodiments may be particularly useful when the insertion device does not penetrate the skin but rather serves as a structural support for the sensor as the sensor is pushed into the skin.

Sensor Control Unit

The sensor control unit can be integrated in the sensor, part or all of which is subcutaneously implanted or it can be configured to be placed on the skin of a patient. The sensor control unit is optionally formed in a shape that is comfortable to the patient and which may permit concealment, for example, under a patient's clothing. The thigh, leg, upper arm, shoulder, or abdomen are convenient parts of the patient's body for placement of the sensor control unit to maintain concealment. However, the sensor control unit may be positioned on other portions of the patient's body. One embodiment of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing typically formed as a single integral unit that rests on the skin of the patient. The housing typically contains most or all of the electronic components of the sensor control unit.

The housing of the sensor control unit may be formed using a variety of materials, including, for example, plastic and polymeric materials, particularly rigid thermoplastics and engineering thermoplastics. Suitable materials include, for example, polyvinyl chloride, polyethylene, polypropylene, polystyrene, ABS polymers, and copolymers thereof. The housing of the sensor control unit may be formed using a variety of techniques including, for example, injection molding, compression molding, casting, and other molding methods. Hollow or recessed regions may be formed in the housing of the sensor control unit. The electronic components of the sensor control unit and/or other items, such as a battery or a speaker for an audible alarm, may be placed in the hollow or recessed areas.

The sensor control unit is typically attached to the skin of the patient, for example, by adhering the sensor control unit directly to the skin of the patient with an adhesive provided on at least a portion of the housing of the sensor control unit which contacts the skin or by suturing the sensor control unit to the skin through suture openings in the sensor control unit.

When positioned on the skin of a patient, the sensor and the electronic components within the sensor control unit are coupled via conductive contacts. The one or more working electrodes, counter electrode (or counter/reference electrode), optional reference electrode, and optional temperature probe are attached to individual conductive contacts. For example, the conductive contacts are provided on the interior of the sensor control unit. Other embodiments of the sensor control unit have the conductive contacts disposed on the exterior of the housing. The placement of the conductive contacts is such that they are in contact with the contact pads on the sensor when the sensor is properly positioned within the sensor control unit.

Sensor Control Unit Electronics

The sensor control unit also typically includes at least a portion of the electronic components that operate the sensor and the analyte monitoring device system. The electronic components of the sensor control unit typically include a power supply for operating the sensor control unit and the sensor, a sensor circuit for obtaining signals from and operating the sensor, a measurement circuit that converts sensor signals to a desired format, and a processing circuit that, at minimum, obtains signals from the sensor circuit and/or measurement circuit and provides the signals to an optional transmitter. In some embodiments, the processing circuit may also partially or completely evaluate the signals from the sensor and convey the resulting data to the optional transmitter and/or activate an optional alarm system if the analyte level exceeds a threshold. The processing circuit often includes digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor control unit may also include digital and/or analog components utilizing semiconductor devices, such as transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

Sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, such as but not limited to glucose concentration and/or temperature and/or rate of change of glucose, etc.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may simply be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit.

Calibration may be accomplished using an in vitro test strip (or other reference), e.g., a small sample test strip such as a test strip that requires less than about 1 microliter of sample (such as, for example FreeStyle® blood glucose monitoring test strips from Abbott Diabetes Care). For example, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Alternative or additional calibration data may be provided based on tests performed by a doctor or some other professional or by the patient. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In some embodiments of the invention, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In some embodiments, the sensor is calibrated only after it has been inserted. In other embodiments, no calibration of the sensor is needed.

Analyte Monitoring Device

In some embodiments of the invention, the analyte monitoring device includes a sensor control unit and a sensor. In these embodiments, the processing circuit of the sensor control unit is able to determine a level of the analyte and activate an alarm system if the analyte level exceeds a threshold. The sensor control unit, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the patient has entered a hyperglycemic state. As another example, a datapoint which correlates to a glucose level of 65 mg/dL exceeds a threshold value for hypoglycemia of 70 mg/dL because the datapoint indicates that the patient is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor. For glucose, the physiologically relevant measurement range is typically about 50 to 250 mg/dL, preferably about 40-300 mg/dL and ideally 30-400 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The subject invention also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

EXAMPLES

Unless indicated otherwise, all of the chemical reagents are available from Aldrich Chemical Co. (Milwaukee, Wis.) or other sources. Additional examples are provided in U.S. Pat. No. 6,605,200 entitled "Polymeric Transition Metal Complexes and Uses Thereof", incorporated herein by reference. For purposes of illustration, the synthesis of several transition metal complex ligands are shown below:

Example 1

Synthesis of 4-(5-carboxypentyl)amino-2,2'-bipyridyl

This example illustrates how a carboxy reactive group is introduced onto a 2,2'-bipyridyl derivative.

Synthesis of compound D: To compound C (formed from A and B according to

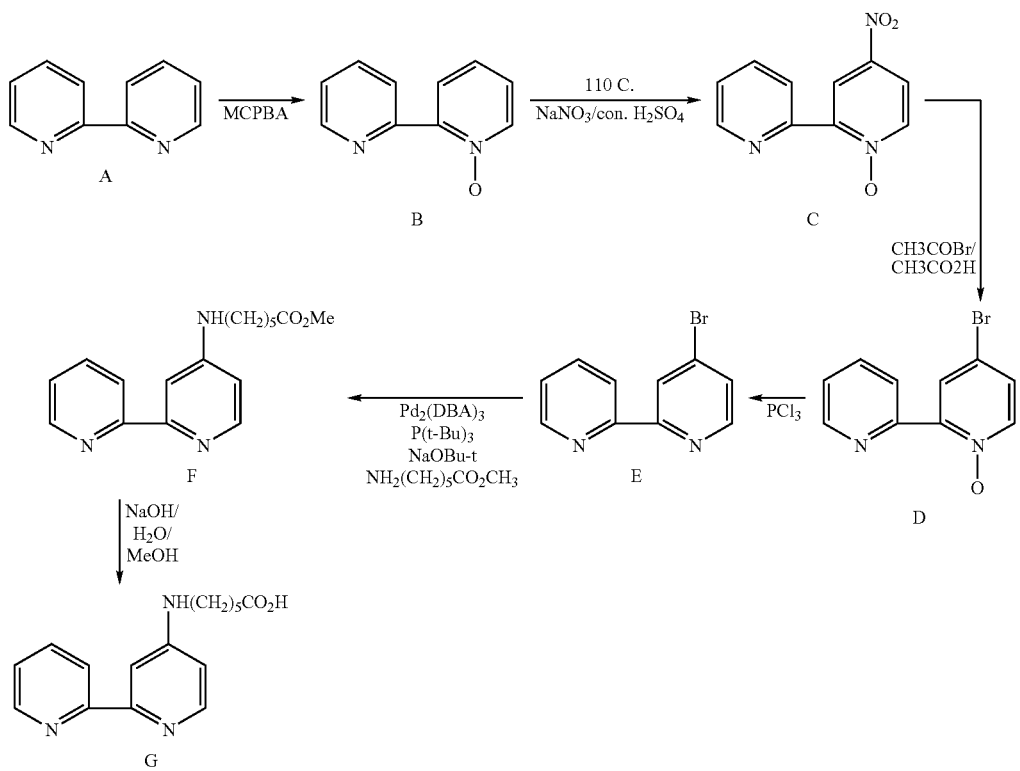

Wenkert, D.; Woodward, R. B. *J. Org. chem.* 48, 283 (1983)) (5 g) dissolved in 30 mL acetic acid in a 100 ml round bottom flask was added 16 mL acetyl bromide. The yellow mixture was refluxed for 1.5 h and then rotovaporated to dryness. The resulting light yellow solid of D was sufficiently pure enough for the next step without further purification. Yield: 95%

Synthesis of compound E: To a stirred suspension of compound D in 60 mL $CHCl_3$ was added 12 mL $PCl_3$ at room temperature. The mixture was refluxed for 2 h under $N_2$ and then cooled to room temperature. The reaction mixture was poured into 100 mL ice/water. The aqueous layer was separated and saved. The $CHCl_3$ layer was extracted three times with $H_2O$ (3×60 mL) and then discarded. The combined aqueous solution was neutralized with $NaHCO_3$ powder to about pH 7 to 8. The resulting white precipitate was collected by suction filtration, washed with $H_2O$ (30 mL) and then dried under vacuum at 50° C. for 24 h. Yield: 85%.

Synthesis of compound F: Compound F was synthesized from compound E (5 g) and 6-aminocaproic acid methyl ester (6 g) using the palladium-catalyzed amination method of aryl bromides described by Hartwig et al. (Hartwig, J. F., et al. *J. Org. Chem.* 64, 5575 (1999)). Yield: 90%.

Synthesis of compound G: Compound F (3 g) dissolved in 20 mL MeOH was added to a solution of NaOH (0.6 g) in 30 mL $H_2O$. The resulting solution was stirred at room temperature for 24 h and then neutralized to pH 7 with dilute HCl. The solution was saturated with NaCl and then extracted with $CHCl_3$. The $CHCl_3$ extract was evaporated to dryness and then purified by a silica gel column eluted with 10% $H_2O$/$CH_3CN$. Yield: 70%.

Example 2

Synthesis of a 4-((6-Aminohexyl)amino)-2,2'-bipyridine

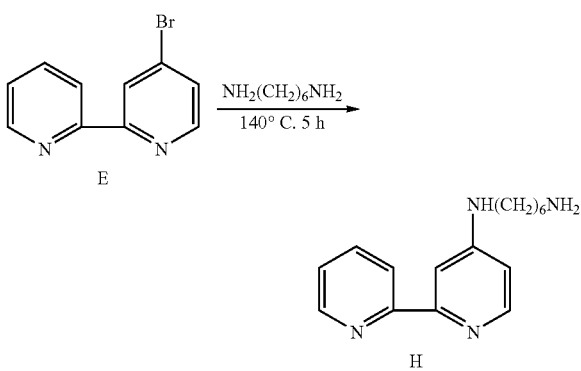

This example illustrates the general synthesis of a 2,2'-bipyridyl with an amine reactive group.

Synthesis of compound H: A mixture of compound E (2.5 g) and 1,6-diaminohexane (15 g) in a 250 mL round bottom flask was heated under $N_2$ at 140° C. in an oil bath for 4-5 h. Excess 1,6-diaminohexane was removed by high vacuum distillation at 90-120° C. The product was purified by a silica gel column, eluting with 5% $NH_4OH$ in isopropyl alcohol. Yield: 70%.

Example 3

Synthesis of 1,1'-dimethyl-2,2'-biimidazole

This example illustrates the synthesis of 2,2'-biimidazole derivatives.

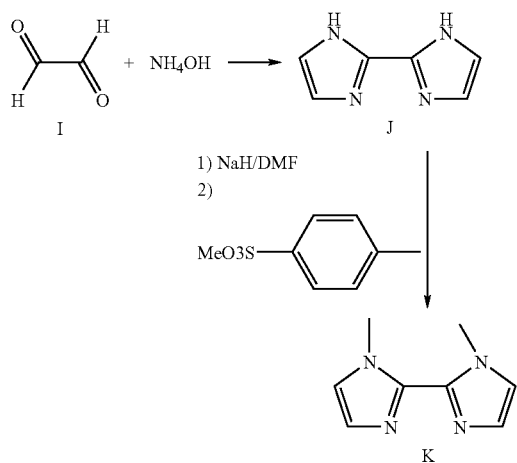

The alkylation step can be carried out stepwise so two different alkyl groups can be introduced. For example:

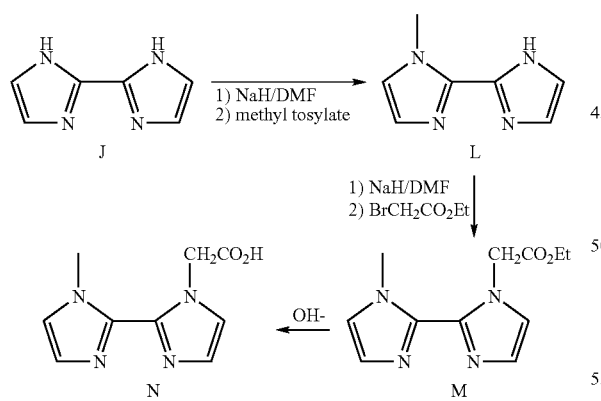

Synthesis of compound K: To a stirred solution of compound J (formed from 1 according to Fieselmann, B. F., et al. Inorg. Chem. 17, 2078 (1978)) (4.6 g, 34.3 mmoles) in 100 mL dry DMF in a 250 ml round bottom flask cooled in an ice/water bath was added in portions NaH(60% in mineral oil, 2.7 g, 68.6 mmoles). After the solution was stirred at 0° C. for one more hour under $N_2$, methyl toluenesulfonate (10.3 mL, 68.6 mmoles) was added in small portions using a syringe over 30 min. The stirring of the solution in the ice/water bath was continued for 1 h and then at room temperature for 3 h. The solvent was removed by vacuum distillation. The dark residue was triturated with ether and then suction filtered and dried under vacuum. The product was purified by sublimation. Yield: 80%.

Synthesis of compound L: Compound L was prepared using the method described for the synthesis of compound K except that only one equivalent each of compound J, NaH and methyl toluenesulfonate was used. The product was purified by sublimation.

Synthesis of compound M: To a stirred solution of compound L (1 g, 6.8 mmoles) in 20 mL dry DMF in a 50 ml round bottom flask cooled in a ice/water bath is added in portions NaH(60% in mineral oil, 0.27 g, 6.8 mmoles). After the solution is stirred at 0° C. for one more hour under $N_2$, ethyl bromoacetate (0.75 mL, 6.8 mmoles) is added in small portions via a syringe over 15 min. The stirring of the solution is continued in the ice/water bath for 1 h and then at room temperature for 3 h. The solvent is removed by vacuum distillation. The product is purified by a silica gel column using 10% $MeOH/CHCl_3$ as the eluent.

Synthesis of Compound N: Compound M (1 g) is hydrolyzed using the method described for the synthesis of compound G. The product is purified by a silica gel column using 10% $H_2O/CH_3CN$ as the eluent.

Example 4

Synthesis of 2-(2-Pyridyl)imidazole Heterobidentate Ligands

This example illustrates a general synthesis of heterobidentate ligands containing an imidazole ring.

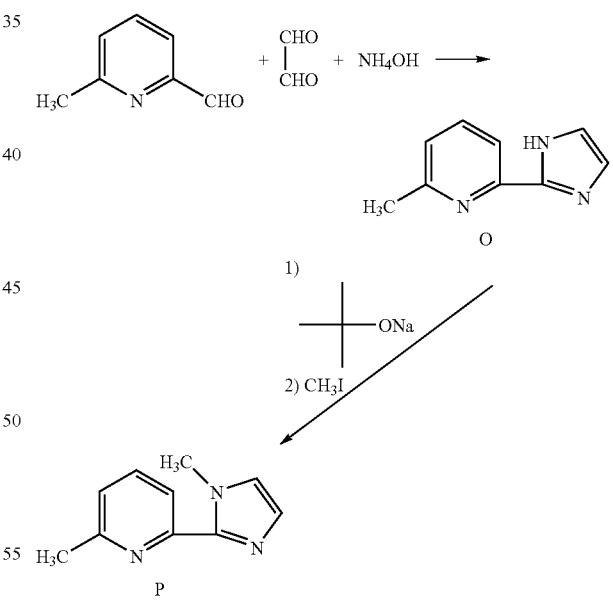

Synthesis of compound O: A solution of 6-methylpyridine-2-carboxaldehyde (26 g, 0.21 mole) and glyoxal (40%, 30 mL) in 50 mL EtOH in a three-necked 250 mL round bottom flask fitted with a thermometer and an addition funnel was stirred in a NaCl/ice bath. When the solution was cooled to below 5° C., conc. $NH_4OH$ was added dropwise through the addition funnel. The rate of the addition was controlled so that the temperature of the solution was maintained at below 5° C. After the addition, the stirring of the yellow solution was continued in the ice bath for 1 h and then at room temperature overnight. The light yellow crystals were collected by suction filtration and washed with $H_2O$ (20 mL). The crystals were resuspended in $H_2O$ (200 mL) and boiled briefly, followed by suction filtration, to collect the product which was dried under high vacuum. Yield: 35%.

Synthesis of compound P: Sodium t-butoxide (2 g, 20.8 mmoles) was added in one portion to a stirred solution of compound O (3 g, 18.9 mmoles) in 50 mL dry DMF. After all of the sodium t-butoxide was dissolved, iodomethane (1.3 mL) was added dropwise using a syringe. The stirring of the solution was continued at room temperature for 2 h and then the solution was poured into $H_2O$ (150 mL). The product was extracted with EtOAc, and the extract was dried with anhydrous $Na_2SO_4$ and then evaporated to give crude compound P. The product was purified by separation on a silica gel column using 10% $MeOH/CHCl_3$ as the eluent. Yield: 70%.

Example 5

Synthesis of Transition Metal Complexes with Multiple Identical Ligands

Transition metal complexes containing multiple identical bidentate or tridentate ligands can be synthesized in one step from a metal halide salt and the ligand. This example illustrates the synthesis of an osmium complex with three identical 2,2'-biimidazole bidentate ligands.

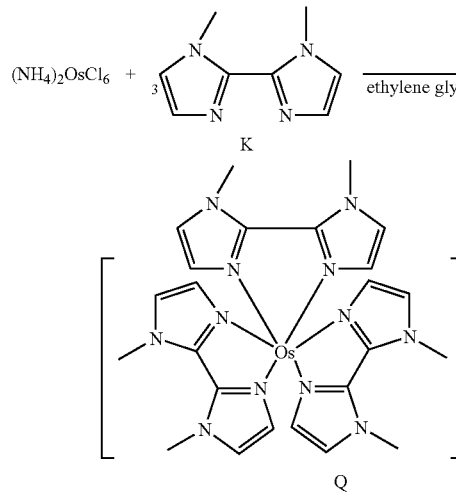

Synthesis of compound Q: Ammonium hexachloroosmate (200 mg, 0.46 mmoles) and compound K (221 mg, 1.37 mmoles) were mixed in 15 mL ethylene glycol in a 100 mL three-necked round bottom flask fitted with a reflux condenser. The mixture was degassed with $N_2$ for 15 min and then stirred under $N_2$ at 200-210° C. for 24 hrs. The solvent was removed by high vacuum distillation at 90-100° C. The green colored crude product was dissolved in 15 mL $H_2O$ and stirred in air to be fully oxidized to the dark blue colored Os(III) oxidation state (about 24 h). The product was purified on a LH-20 reverse phase column using $H_2O$ as the eluent. Yield: 50%.

Example 6

Synthesis of Transition Metal Complexes with Mixed Ligands

Transition metal complexes containing multiple types of ligands can be synthesized stepwise. First, a transition metal complex intermediate that contains one desired type of ligand and halide ligand(s), for example, chloride, is synthesized. Then the intermediate is subjected to a ligand substitution reaction to displace the halide ligand(s) with another desired type of ligand. The preparation of the following osmium complex illustrates the general synthetic scheme.

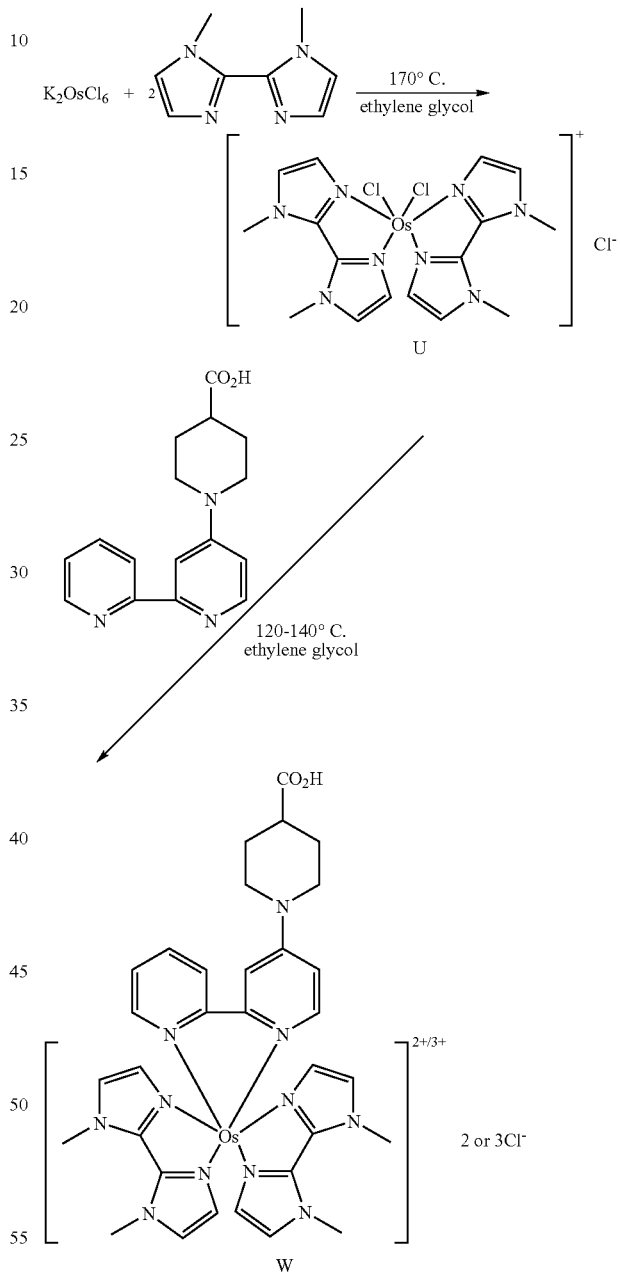

Synthesis of Compound U: Potassium hexachloroosmate (1 g, 2.08 mmoles), compound K (0.67 g, 4.16 mmoles) and LiCl (1 g, 23.8 mmoles) were suspended in 40 mL ethylene glycol in a 250 mL three-necked round bottom flask fitted with a reflux condenser. The suspension was degassed with $N_2$ for 15 min and then stirred under $N_2$ at 170° C. in an oil bath for 7-8 h, resulting in a dark brown solution. The solvent was removed by high vacuum distillation at 90-100° C. bath temperature. The gummy solid was triturated with acetone twice (2×50 mL) and then with H$_2$O once (50 mL). The product was dried at 50° C. under high vacuum for 24 h.

Synthesis of compound W: A suspension of compound U (119 mg, 0.192 mmole) and 4-(4-carboxypiperidino)amino-2,2'-bipyridyl (prepared from compound E and ethyl isonipecotate using the synthetic methods for compounds F and G) was made in 10 mL ethylene glycol in a 100 mL three-necked round bottom flask equipped with a reflux condenser. The suspension was degassed with N$_2$ for 15 min and then stirred under N$_2$ at 130° C. in an oil bath for 24 h. The dark brown solution was cooled to room temperature and then poured into EtOAc (50 mL). The precipitate was collected by suction filtration. The dark brown solid thus obtained was compound W with osmium in a 2+ oxidation state. For ease of purification, the osmium 2+ complex was oxidized to an osmium 3+ complex by dissolving the dark brown solid in 20 mL H$_2$O and stirring the solution in open air for 24 h. The resulting dark green solution was poured into a stirred solution of NH$_4$PF$_6$ (1 g) in 20 mL H$_2$O. The resulting dark green precipitate of [Os(1,1'-dimethyl-2,2'-biimidazole)$_2$(4-(4-carboxypiperidino)amino-2,2'-bipyridyl)]$^{3+}$3 PF$_6^-$ was collected by suction filtration and washed with 5 mL H$_2$O and then dried at 40° C. under high vacuum for 48 h. The counter anion PF$_6^-$ of [Os(1,1'-dimethyl-2,2'-biimidazole)$_2$(4-(4-carboxypiperidino)amino-2,2'-bipyridyl)]$^{3+}$3 PF$_6^-$ was exchanged to the more water soluble chloride anion. A suspension of the PF$_6^-$ salt of compound W (150 mg) and Cl$^-$ resin (10 mL) in H$_2$O (20 mL) was stirred for 24 h, at the end of which period all of osmium complex was dissolved. The dark green solution was separated by suction filtration and then lyophilized to give compound W.

Example 7

Electrochemical Sensor Using an Analyte Responsive Dehydrogenase

An electrochemical analyte sensor was constructed using a dehydrogenase based on the formulation provided in Table 3.

TABLE 3

Sensing layer chemistry formulation

| Component | | Volume Ratio |
|---|---|---|
| Redox polymer (X7) | All 20 mg/ml in | 0.05 |
| FADGDH | 10 mM Hepes buffer, | 0.12 |
| PEGDGE 400 | pH = 8 | 0.044 |

The three component of the sensing layer were dissolved in Hepes buffer at 20 mg/ml and were mixed according to the volume ration noted in Table 4 and the resulting solution was rocked for 30 minutes. A 25 mL volume of the sensing layer chemistry formulation was then deposited on a carbon working electrode of a Navigator™ sensor using a microsyringe. The electrochemical sensor was then left at ambient lab environment to for 2 days. Following the curing, the electrochemical sensor was then ready for use.

Figure 6:
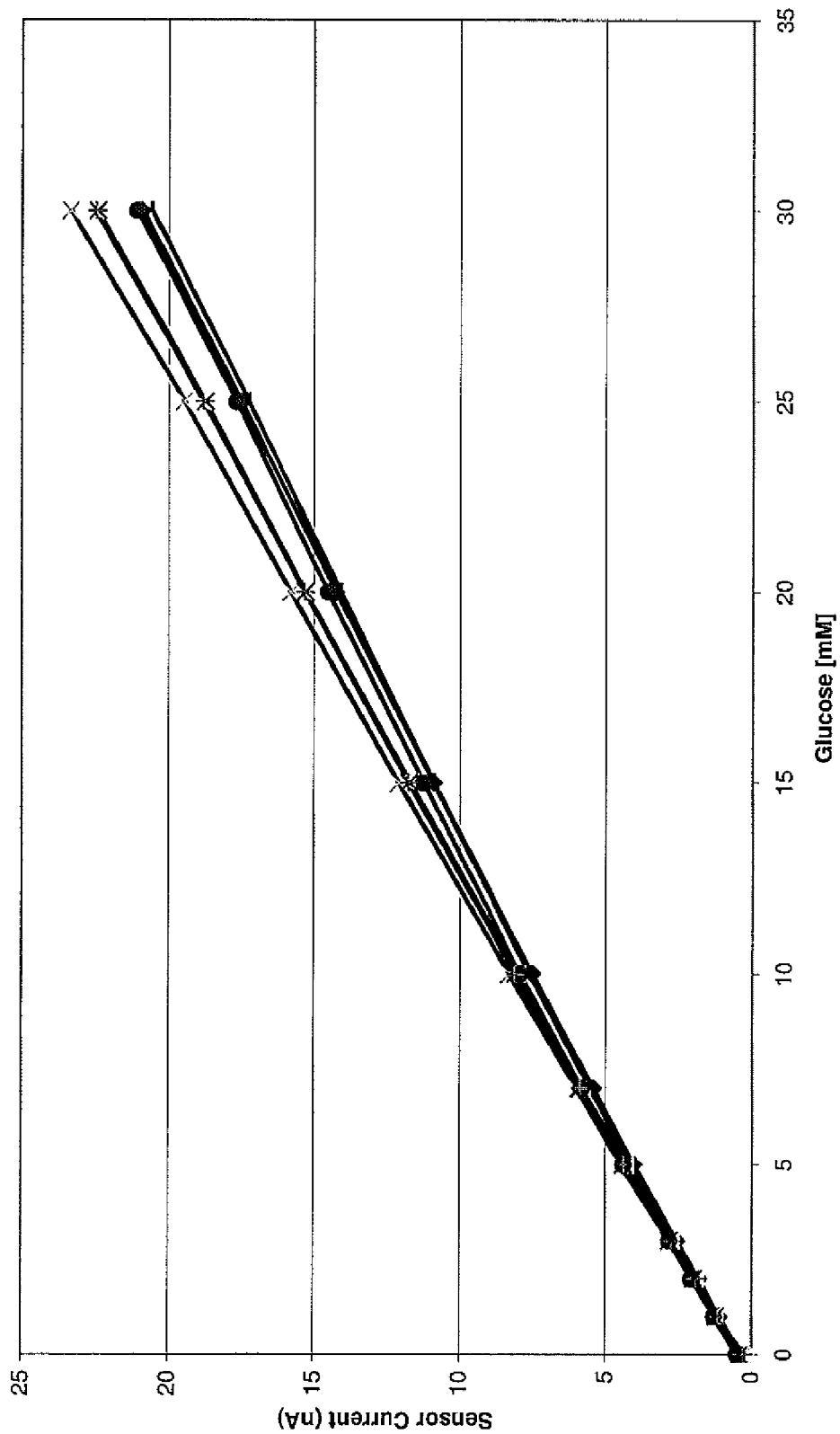
FIG. 6 is a graph showing the calibration of an FAD-GDH-based sensor of an embodiment of the invention. Glucose is presented on the x-axis at increasing concentrations in milimolar (mM). Sensor current is shown on the y-axis at increasing levels in nanoamperes (nA). The sensors prepared according to the methods described herein were tested in PBS at 37° C. As can be seen in FIG. 6, the sensors showed excellent linearity.
Figure 7:
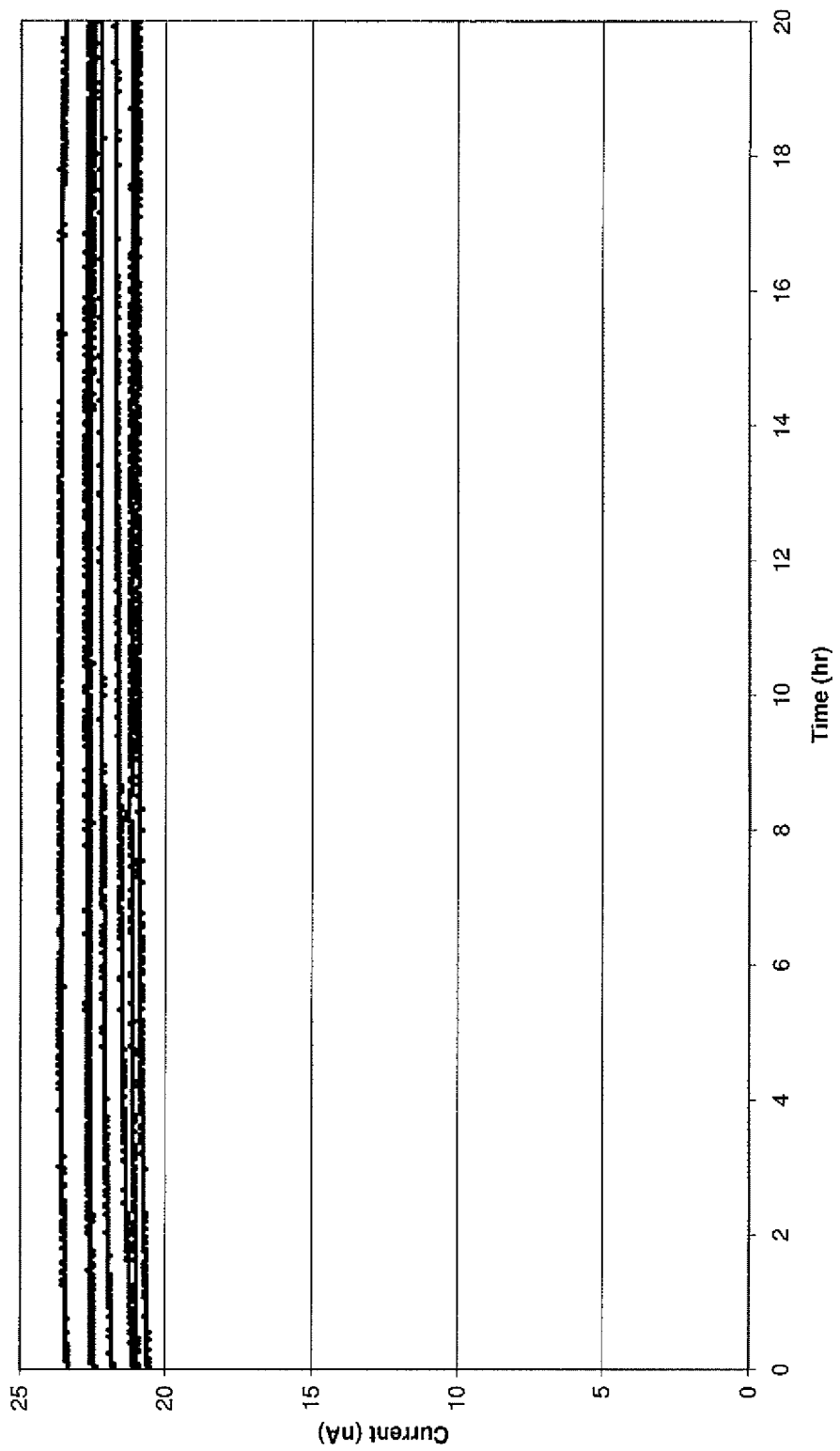
FIG. 7 is a graph showing the beaker stability of an FAD-GDH-based sensor of an embodiment of the invention. Glucose is presented on the x-axis at increasing concentrations in milimolar (mM). Sensor current is shown on the y-axis at increasing levels in nanoamperes (nA). The sensors prepared according to the methods described herein were tested in PBS at 37° C. As can be seen in FIG. 7, the sensors showed excellent stability.
Figure 8:
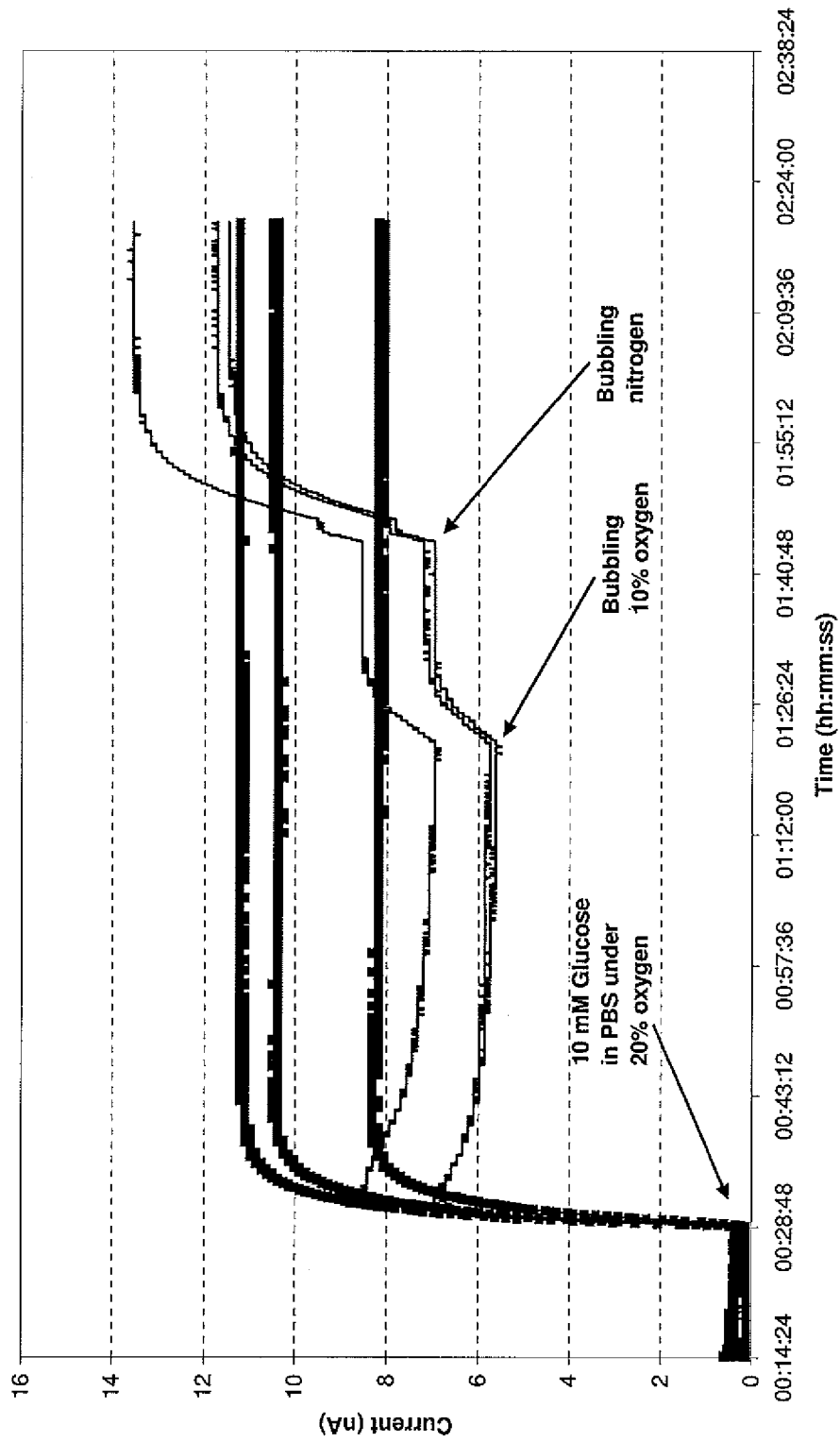
FIG. 8 is a graph showing that FAD-GDH-based sensors of an embodiment of the invention are free of an "oxygen-effect" (within the sensitivity to the equipment used here) while regular GOx-based sensors are affected by varying oxygen concentrations.

The electrochemical analyte sensors were then tested in PBS at 37° C. The sensors showed excellent linearity and stability, as shown in FIGS. 6 and 7. Oxygen interference tests were subsequently performed on the fabricated sensors as well as traditional Navigator™ sensors employing glucose oxidase. FIG. 8 shows that FADGDH-based electrochemical analyte sensors (thick lines) performed free of an oxygen effect, as indicated by the constant currents during the change in oxygen concentration. Traditional GOx-based electrochemical analyte sensors (thin lines) showed significant current increase when oxygen concentrations were decreased, as exemplified by the bubbling of 10% oxygen, as well as the bubbling of nitrogen. As shown in FIG. 8, the three FADGDH-based electrochemical analyte sensors (thick lines) maintained constant current during the change in oxygen concentration, while the current of the GOx-based electrochemical analyte sensors (thin lines) significantly changed upon the change in oxygen concentration.

Therefore, based on these results, the electrochemical analyte sensors of the embodiments of the invention having an oxygen-effect free advantage can be use used in vivo, ex-vivo, and in-vitro, including subcutaneous implantation in a subject, for analysis of analyte levels.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the embodiments of the invention, therefore, is not intended to be limited to the exemplary embodiments shown and described herein. Rather, the scope and spirit of the embodiments of the invention is embodied by the appended claims.

That which is claimed is:

1. An electrochemical sensor, comprising:
a substrate comprising a working electrode and a counter electrode;
a co-factor associated dehydrogenase disposed on the working electrode, wherein the dehydrogenase reacts with an analyte of interest resulting in generation of free electrons; and
a redox mediator disposed proximate to the working electrode that assists in the transfer of the free electrons to the working electrode, wherein the redox mediator comprises a transition metal complex having the following formula:

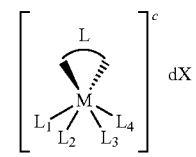

wherein
(i) M is ruthenium, osmium, or vanadium; and
(ii) L is selected from the group consisting of:

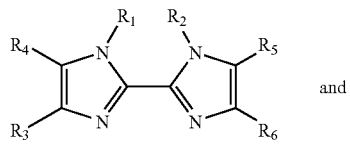

and

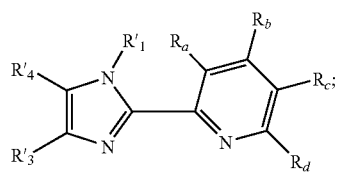

wherein:

$R_1$, $R_2$, and $R'_1$ are independently substituted or unsubstituted alkyl, alkenyl, alkoxy, alkylamino, alkylthio or aryl groups;

$R_3$, $R_4$, $R_5$, $R_6$, $R'_3$, $R'_4$, $R_a$, $R_b$, $R_c$, and $R_d$ are independently —H, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino, alkylthio, alkenyl, aryl, or alkyl;

c is an integer selected from −1 to −5 or +1 to +5 indicating a positive or negative charge;

X represents at least one counter ion;

d is an integer from 1 to 5 representing the number of counter ions; and $L_1$, $L_2$, $L_3$ and $L_4$ are ligands, wherein at least one of $R_1$, $R_2$, and $R'_1$ is coupled a polymeric backbone; and wherein $L_1$ and $L_2$ in combination form a first bidentate ligand.

2. The sensor of claim 1, wherein at least a portion of the sensor is adapted to be subcutaneously positioned in a subject.

3. The sensor of claim 1, wherein the dehydrogenase is glucose dehydrogenase.

4. The sensor of claim 1, wherein the co-factor is flavin adenine dinucleotide (FAD), nicotinamide adenine dinucleotide (NAD), or pyrroloquinoline quinone (PQQ).

5. The sensor of claim 1, wherein the dehdrogenase comprises a complex of glucose dehydrogenase (GDH) and flavin adenine dinucleotide (FAD).

6. The sensor of claim 1, wherein the substrate further comprises a reference electrode.

7. The sensor of claim 1, further comprising a polymeric membrane on the working electrode.

8. The sensor of claim 1, wherein the redox mediator further comprises a polymeric backbone and a cross-linker.

9. The sensor of claim 8, wherein the polymeric backbone comprises a poly(vinylpyridine) having the following general structure, where n is 2, n' is 17, and n" is 1:

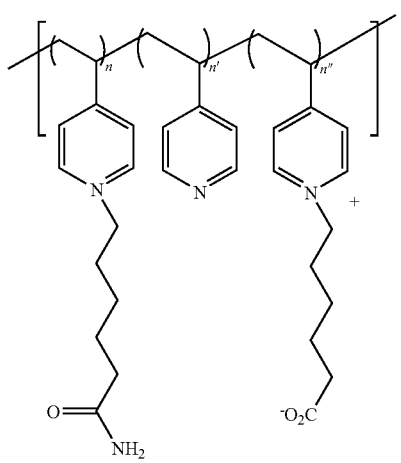

10. The sensor of claim 8, wherein the cross-linker is polyethylene glycol diglycidyl ether (PEGDGE) having the following general formula:

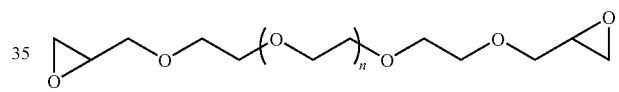

wherein n is from about 0 to about 50.

11. The sensor of claim 8, wherein the redox mediator has the following structure:

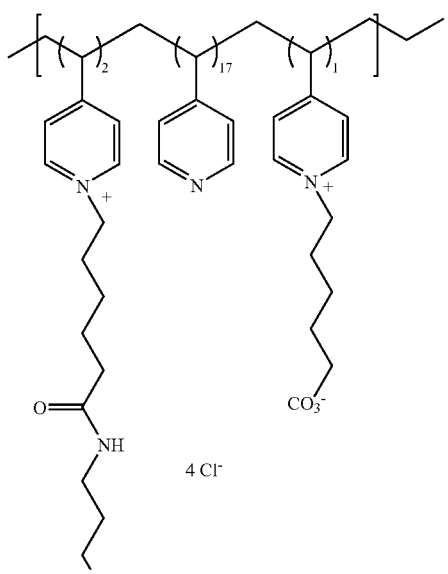

-continued

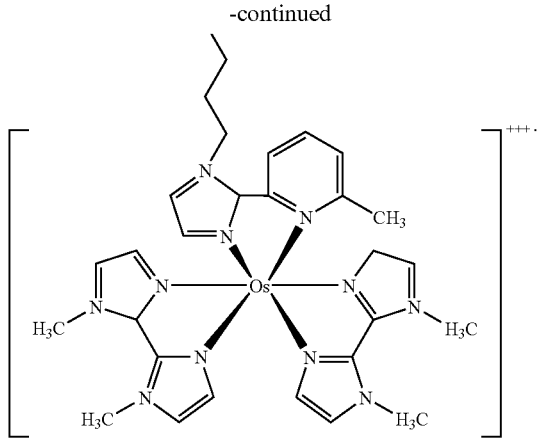

12. The sensor of claim 8, wherein the polymeric backbone comprises a poly(vinylpyridine-co-styrene) copolymer.

13. The sensor of claim 12, wherein the poly(vinylpyridine-co-styrene) copolymer is derivitized by the addition of propylsulfonate and poly(ethyleneoxide) moieties.

14. The sensor of claim 12, wherein the poly(vinylpyridine-co-styrene) copolymer has the following structure:

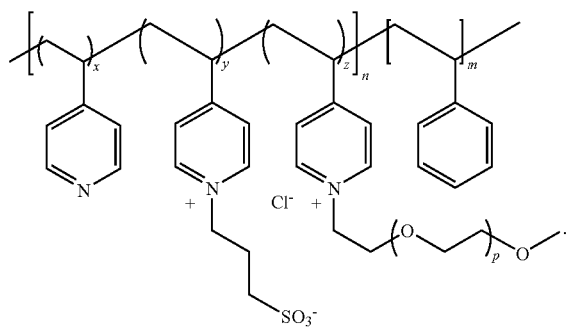

15. The sensor of claim 12, wherein the polymeric backbone comprises:
a cross-linker; and
a copolymer having the following general structure:

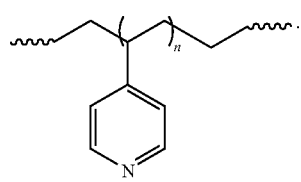

16. The sensor of claim 8, wherein the cross-linker is triglycidyl glycerol.

17. The sensor of claim 1, wherein the transition metal complex comprises the following formula:

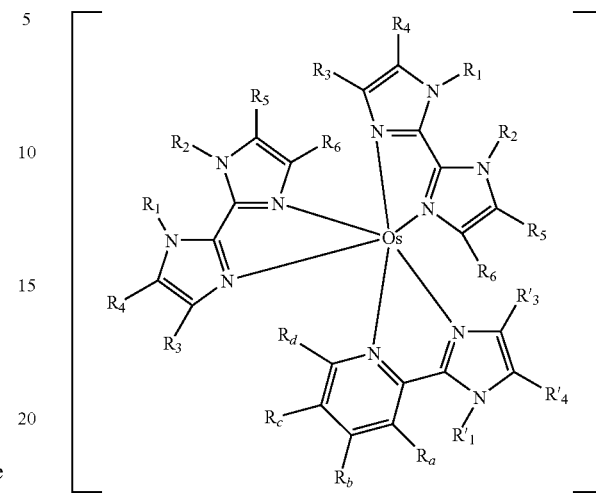

wherein $R_3$, $R_4$, $R_5$, $R_6$, $R_a$, $R_b$, $R_c$, $R_d$, $R'_3$ and $R'_4$ are —H; and $R_1$, $R_2$, and $R'_1$ are independently -H or substituted or unsubstituted C1-C12 alkoxy, C1-12 alkylthio, C1-C12 alkylamino, C2-C24 dialkylamino, or C1-C12 alkyl.

18. The sensor of claim 17, wherein at least one of $R_1$, $R_2$, and $R'_1$ further comprises a reactive group selected from the group consisting of carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxyamine, alkyl halide, imidazole, pyridine, phenol, alkyl sulfonate, halotriazine, imido ester, maleimide, hydrazide, hydroxy, and photo-reactive azido aryl groups.

19. An analyte sensor assembly, comprising:
an electrochemical sensor comprising:
a substrate comprising a working electrode and a counter electrode,
a working electrode comprising a dehydrogenase disposed thereon, wherein the dehydrogenase reacts with an analyte of interest resulting in generation of free electrons; and
a redox mediator disposed proximate to the working electrode that assists in the transfer of the free electrons to the working electrode, wherein the redox mediator comprises a transition metal complex having the following formula:

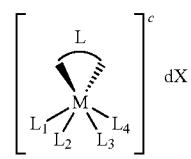

wherein
(i) M is ruthenium, osmium, or vanadium; and
(ii) L is selected from the group consisting of:

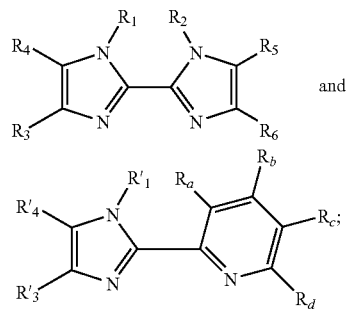

and wherein:
$R_1$, $R_2$, and $R'_1$ are independently substituted or unsubstituted alkyl, alkenyl, alkoxy, alkylamino, alkylthio or aryl groups;
$R_3$, $R_4$, $R_5$, $R_6$, $R'_3$, $R'_4$, $R_a$, $R_b$, $R_c$, and $R_d$ are independently —H, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino, alkylthio, alkenyl, aryl, or alkyl;
c is an integer selected from −1 to −5 or +1 to +5 indicating a positive or negative charge;
X represents at least one counter ion;
d is an integer from 1 to 5 representing the number of counter ions; and
$L_1$, $L_2$, $L_3$ and $L_4$ are ligands,
wherein at least one of $R_1$, $R_2$, and $R'_1$ is coupled a polymeric backbone;
and wherein $L_1$ and $L_2$ in combination form a first bidentate ligand; and
a transmitter unit operatively coupled to the electrochemical sensor and configured to receive one or more signals from the electrochemical sensor corresponding to an analyte level of a subject.

20. The analyte sensor assembly of claim 19, wherein at least a portion of the sensor is adapted to be subcutaneously positioned in the subject.

21. The analyte sensor assembly of claim 19, wherein the dehydrogenase is glucose dehydrogenase.

22. The analyte sensor assembly of claim 19, wherein glucose dehydrogenase is associated with a co-factor.

23. The analyte sensor assembly of claim 22, wherein the co-factor is flavin adenine dinucleotide (FAD), nicotinamide adenine dinucleotide (NAD), or pyrroloquinoline quinone (PQQ).

24. The analyte sensor assembly of claim 19, wherein the dehydrogenase comprises a complex of glucose dehydrogenase (GDH) and flavin adenine dinucleotide (FAD).

25. The analyte sensor assembly of claim 19, wherein the substrate further comprises a reference electrode.

26. The analyte sensor assembly of claim 19, further comprising a polymeric membrane on the electrode.

27. The sensor of claim 19, wherein the redox mediator further comprises a polymeric backbone and a cross-linker.

28. The sensor of claim 27, wherein the polymeric backbone comprises a poly(vinylpyridine) having the following general structure, where n may be 2, n' is 17, and n" is 1:

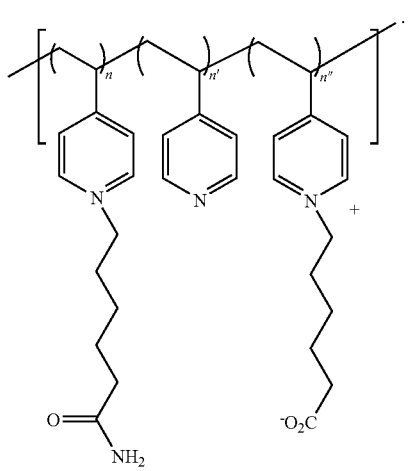

29. The sensor of claim 27, wherein the cross-linker is polyethylene glycol diglycidyl ether (PEGDGE) having the following general formula:

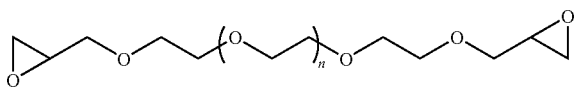

wherein n is from about 0 to about 50.

30. The sensor of claim 27, wherein the redox mediator has the following structure:

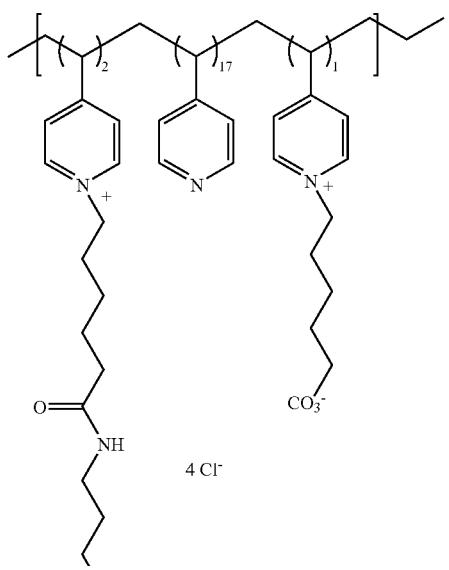

-continued

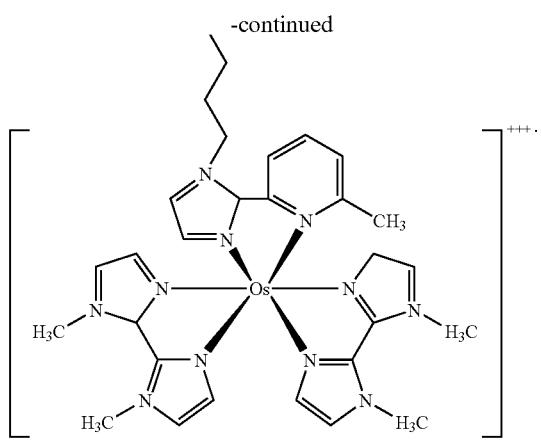

31. The sensor of claim 27, wherein the polymeric backbone comprises a poly(vinylpyridine-co-styrene) copolymer.

32. The sensor of claim 31, wherein the poly(vinylpyridine-co-styrene) copolymer is derivitized by the addition of propylsulfonate and poly(ethyleneoxide) moieties.

33. The sensor of claim 31, wherein the poly(vinylpyridine-co-styrene) copolymer has the following structure:

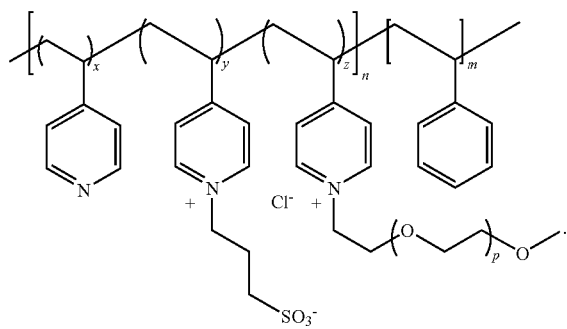

34. The sensor of claim 31, wherein the polymeric backbone comprises:
a cross-linker; and
a copolymer having the following general structure:

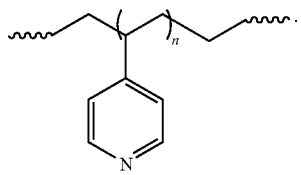

35. The sensor of claim 27, wherein the cross-linker is triglycidyl glycerol.

36. The sensor of claim 19, wherein the transition metal complex comprises the following formula:

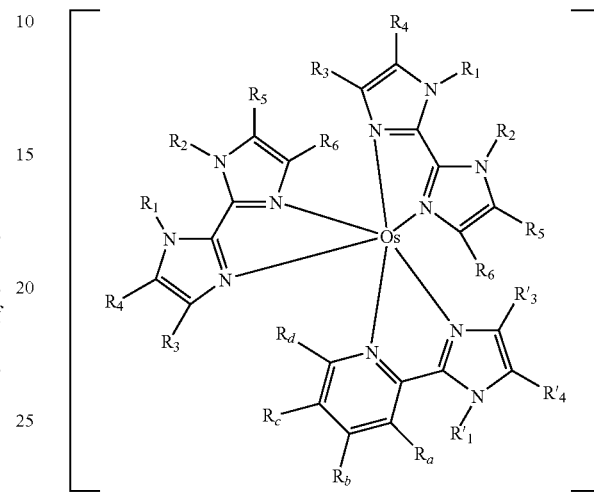

wherein $R_3$, $R_4$, $R_5$, $R_6$, $R_a$, $R_b$, $R_c$, $R_d$, $R'_3$ and $R'_4$ are —H; and $R_1$, $R_2$, and $R'_1$ are independently —H or substituted or unsubstituted C1-C12 alkoxy, C1-12 alkylthio, C1-C12 alkylamino, C2-C24 dialkylamino, or C1-C12 alkyl.

37. The sensor of claim 36, wherein at least one of $R_1$, $R_2$, and $R'_1$ further comprises a reactive group selected from the group consisting of carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxyamine, alkyl halide, imidazole, pyridine, phenol, alkyl sulfonate, halotriazine, imido ester, maleimide, hydrazide, hydroxy, and photo-reactive azido aryl groups.

38. The sensor of claim 37, wherein at least one of $R_1$, $R_2$, and $R'_1$ is coupled to a polymeric backbone.

* * * * *